(12) United States Patent
LaFrance et al.

(10) Patent No.: US 11,578,044 B2
(45) Date of Patent: Feb. 14, 2023

(54) CRYSTALLINE FORMS OF ERAVACYCLINE

(71) Applicant: Tetraphase Pharmaceuticals, Inc., Watertown, MA (US)

(72) Inventors: Danny LaFrance, Natick, MA (US); Philip C. Hogan, Brighton, MA (US); Yansheng Liu, Winchester, MA (US); Minsheng He, Andover, MA (US); Chi-Li Chen, Newton, MA (US); John Niu, Bedford, MA (US)

(73) Assignee: Tetraphase Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 17/188,063

(22) Filed: Mar. 1, 2021

(65) Prior Publication Data

US 2021/0363103 A1 Nov. 25, 2021

Related U.S. Application Data

(63) Continuation of application No. 16/342,779, filed as application No. PCT/US2017/057385 on Oct. 19, 2017, now Pat. No. 10,961,190.

(60) Provisional application No. 62/410,230, filed on Oct. 19, 2016.

(51) Int. Cl.
  *A61P 31/04* (2006.01)
  *C07D 295/15* (2006.01)
  *C07D 207/06* (2006.01)

(52) U.S. Cl.
  CPC ............ *C07D 295/15* (2013.01); *A61P 31/04* (2018.01); *C07D 207/06* (2013.01); *C07B 2200/13* (2013.01)

(58) Field of Classification Search
  None
  See application file for complete search history.

(56) References Cited

U.S. PATENT DOCUMENTS

| | | | |
|---|---|---|---|
| 3,226,436 A | 12/1965 | Petlsi et al. |
| 3,247,226 A | 4/1966 | Esse et al. |
| 3,338,963 A | 8/1967 | Petisi et al. |
| 3,364,123 A | 1/1968 | Neidleman |
| 3,394,178 A | 7/1968 | Dulaney et al. |
| 3,433,709 A | 3/1969 | McCormick et al. |
| 3,824,285 A | 7/1974 | Blackwood et al. |
| 3,849,493 A | 11/1974 | Conover et al. |
| 3,947,517 A | 3/1976 | Muxfeldt et al. |
| 3,988,468 A | 10/1976 | Rogalski et al. |
| 4,024,272 A | 5/1977 | Rogalski et al. |
| 4,160,783 A | 7/1979 | Cakara et al. |
| 5,284,963 A | 2/1994 | Sum et al. |
| 5,328,902 A | 7/1994 | Sum et al. |
| 5,380,888 A | 1/1995 | Sum et al. |
| 5,386,041 A | 1/1995 | Sum et al. |
| 5,401,729 A | 3/1995 | Sum et al. |
| 5,430,162 A | 7/1995 | Sum et al. |
| 5,442,059 A | 8/1995 | Sum et al. |
| 5,466,684 A | 11/1995 | Sum et al. |
| 5,494,903 A | 2/1996 | Hlavka et al. |
| 5,495,031 A | 2/1996 | Sum et al. |
| 5,529,990 A | 6/1996 | Hlavka et al. |
| 5,530,117 A | 6/1996 | Hlavka et al. |
| 5,574,026 A | 11/1996 | Backer et al. |
| 5,668,122 A | 9/1997 | Fife et al. |
| 5,843,925 A | 12/1998 | Backer et al. |
| 6,100,248 A | 8/2000 | Golub et al. |
| 6,277,061 B1 | 8/2001 | Golub et al. |
| 6,683,068 B2 | 1/2004 | Nelson et al. |
| 6,841,546 B2 | 1/2005 | Draper et al. |
| 6,914,057 B1 | 7/2005 | Ryan et al. |
| 7,045,507 B2 | 5/2006 | Draper et al. |
| RE40,086 E | 2/2008 | Hlavka et al. |
| RE40,183 E | 3/2008 | Hlavka et al. |
| 7,763,735 B2 | 7/2010 | Myers et al. |
| 7,807,842 B2 | 10/2010 | Myers et al. |
| 7,820,641 B2 | 10/2010 | Nelson et al. |
| 7,825,105 B2 | 11/2010 | Bandarage et al. |

(Continued)

FOREIGN PATENT DOCUMENTS

| CN | 1072172 A | 5/1993 |
|---|---|---|
| CN | 1083047 A | 3/1994 |

(Continued)

OTHER PUBLICATIONS

"The Tetracyclines: Handbook of Experimental Pharmacology," 78: 125-275 (1985).

(Continued)

*Primary Examiner* — Joseph R Kosack
(74) *Attorney, Agent, or Firm* — Foley Hoag LLP

(57) ABSTRACT

The invention relates to crystalline forms of the bis-HCl salt of a compound represented by Structural Formula 1, and pharmaceutical compositions comprising crystalline forms of the bis-HCL salt of a compound represented by Structural Formula 1 described herein. The crystalline forms of the bis-HCl salt of a compound of Structural Formula 1 and compositions comprising the crystalline forms of the compound of Structural Formula 1 provided herein, in particular, crystalline Form I, crystalline Form J, crystalline Form A, and crystalline Form B, or mixtures thereof, can be incorporated into pharmaceutical compositions, which can be used to treat various disorders. Also described herein are methods for preparing the crystalline forms (e.g., Forms I, J, B and A) of the bis-HCl salt of a compound represented by Structural Formula 1.

20 Claims, 17 Drawing Sheets

(56) References Cited

U.S. PATENT DOCUMENTS

| | | |
|---|---|---|
| 7,939,513 B2 | 5/2011 | Takhi et al. |
| 8,088,820 B2 | 1/2012 | Draper et al. |
| 8,367,654 B2 | 2/2013 | Clark et al. |
| 8,501,716 B2 | 8/2013 | Zhou et al. |
| 8,796,245 B2 | 8/2014 | Zhou et al. |
| 8,828,988 B2 | 9/2014 | Clark et al. |
| 8,906,887 B2 | 12/2014 | Zhou et al. |
| 9,315,451 B2 | 4/2016 | Chen et al. |
| 9,371,283 B2 | 6/2016 | Xiao et al. |
| 9,522,872 B2 | 12/2016 | Seyedi et al. |
| 9,533,943 B2 | 1/2017 | Bowser et al. |
| 9,562,003 B2 | 2/2017 | Levy et al. |
| 9,573,895 B2 | 2/2017 | Xiao et al. |
| 9,624,166 B2 | 4/2017 | Deng et al. |
| 10,072,007 B2 | 9/2018 | Chen et al. |
| 10,315,992 B2 | 6/2019 | Xiao et al. |
| 10,913,712 B2 | 2/2021 | Xiao et al. |
| 10,961,190 B2 | 3/2021 | LaFrance et al. |
| 2004/0063674 A1 | 4/2004 | Levy et al. |
| 2004/0092490 A1 | 5/2004 | Draper et al. |
| 2004/0214800 A1 | 10/2004 | Levy et al. |
| 2004/0224928 A1 | 11/2004 | Nelson et al. |
| 2004/0242548 A1 | 12/2004 | Draper et al. |
| 2005/0143352 A1 | 6/2005 | Nelson et al. |
| 2006/0166944 A1 | 7/2006 | Berniac et al. |
| 2006/0166945 A1 | 7/2006 | Abato et al. |
| 2006/0183720 A1 | 8/2006 | Sum et al. |
| 2006/0194773 A1 | 8/2006 | Levy et al. |
| 2006/0281717 A1 | 12/2006 | Berniac et al. |
| 2007/0093455 A1 | 4/2007 | Abato et al. |
| 2008/0015169 A1 | 1/2008 | Nelson et al. |
| 2008/0070873 A1 | 3/2008 | Alekshun et al. |
| 2008/0118979 A1 | 5/2008 | Draper et al. |
| 2009/0118269 A1 | 5/2009 | Berniac et al. |
| 2009/0257985 A1 | 10/2009 | Nelson et al. |
| 2010/0022483 A1 | 1/2010 | Berniac et al. |
| 2010/0105671 A1 | 4/2010 | Zhou et al. |
| 2011/0009371 A1 | 1/2011 | Myers et al. |
| 2011/0269714 A1 | 11/2011 | Xiao et al. |
| 2012/0108569 A1 | 5/2012 | Clark et al. |
| 2012/0135968 A1 | 5/2012 | Chen et al. |
| 2012/0208788 A1 | 8/2012 | Deng et al. |
| 2012/0302527 A1 | 11/2012 | Zhou et al. |
| 2012/0329761 A1 | 12/2012 | Schimmer et al. |
| 2013/0109657 A1 | 5/2013 | Zhou et al. |
| 2013/0345178 A1 | 12/2013 | Clark et al. |
| 2015/0274643 A1 | 10/2015 | Zhou et al. |
| 2016/0107988 A1 | 4/2016 | Xiao et al. |
| 2017/0044160 A1 | 2/2017 | Chen et al. |
| 2017/0107179 A1 | 4/2017 | Xiao et al. |
| 2017/0275244 A1 | 9/2017 | Zhou et al. |
| 2017/0283368 A1 | 10/2017 | Seyedi et al. |
| 2017/0305852 A1 | 10/2017 | Xiao et al. |
| 2017/0334841 A1 | 11/2017 | Deng et al. |
| 2020/0048193 A1 | 2/2020 | Xiao et al. |
| 2020/0055813 A1 | 2/2020 | Zhou et al. |

FOREIGN PATENT DOCUMENTS

| | | |
|---|---|---|
| CN | 1087626 A | 6/1994 |
| CN | 1090267 A | 8/1994 |
| CN | 1034216 C | 3/1997 |
| CN | 1653037 A | 8/2005 |
| CN | 1845897 A | 10/2006 |
| CN | 101010315 A | 8/2007 |
| CN | 101027279 A | 8/2007 |
| EP | 0 536 515 A1 | 4/1993 |
| EP | 0 582 789 A1 | 2/1994 |
| EP | 0 582 810 A1 | 2/1994 |
| EP | 0 618 190 A1 | 10/1994 |
| EP | 230 1916 A2 | 3/2011 |
| GB | 935 384 A | 8/1963 |
| GB | 1 034 933 A | 7/1966 |
| GB | 1065716 A | 4/1967 |
| GB | 1077598 A | 8/1967 |
| GB | 1563663 A | 3/1980 |
| JP | S5141362 A | 4/1976 |
| JP | H05255219 | 10/1993 |
| JP | H07309823 A | 11/1995 |
| JP | 2004502753 A | 1/2004 |
| JP | 2005520846 A | 7/2005 |
| JP | 2008530106 A | 8/2008 |
| JP | 2015-528468 A | 9/2015 |
| TW | 275616 B | 5/1996 |
| TW | I299038 B | 7/2008 |
| TW | I508934 B | 11/2015 |
| WO | WO-99/37307 A1 | 7/1999 |
| WO | WO-00/18353 A2 | 4/2000 |
| WO | WO-01/98260 A1 | 12/2001 |
| WO | WO-2002/04404 A2 | 1/2002 |
| WO | WO-2002/04407 A2 | 1/2002 |
| WO | WO-2002/072022 A2 | 9/2002 |
| WO | WO-2002/072031 A2 | 9/2002 |
| WO | WO-2002/085303 A2 | 10/2002 |
| WO | WO-2003/005971 A2 | 1/2003 |
| WO | WO-2003/057169 A2 | 7/2003 |
| WO | WO-2003/079984 A2 | 10/2003 |
| WO | WO-2004/006850 A2 | 1/2004 |
| WO | WO-2004/038000 A2 | 5/2004 |
| WO | WO-2004/038001 A2 | 5/2004 |
| WO | WO-2005/009943 A2 | 2/2005 |
| WO | WO-2005/082860 A1 | 9/2005 |
| WO | WO-2005/112945 A2 | 12/2005 |
| WO | WO-2006/047671 A2 | 5/2006 |
| WO | WO-2006/047756 A2 | 5/2006 |
| WO | WO-2006/084265 A1 | 8/2006 |
| WO | WO-2006/088720 A2 | 8/2006 |
| WO | WO-2007/014154 A2 | 2/2007 |
| WO | WO-2007/087416 A2 | 8/2007 |
| WO | WO-2007/117639 A2 | 10/2007 |
| WO | WO-2007/133798 A2 | 11/2007 |
| WO | WO-2008/045507 A2 | 4/2008 |
| WO | WO-2008/079339 A2 | 7/2008 |
| WO | WO-2008/127361 A2 | 10/2008 |
| WO | WO-2008/127722 A1 | 10/2008 |
| WO | WO-2009/073056 A1 | 6/2009 |
| WO | WO-2009/128913 A1 | 10/2009 |
| WO | WO-2010/006292 A1 | 1/2010 |
| WO | WO-2010/017470 A1 | 2/2010 |
| WO | WO-2010/126607 A2 | 11/2010 |
| WO | WO-2010/129055 A1 | 11/2010 |
| WO | WO-2010/129057 A2 | 11/2010 |
| WO | WO-2010/132670 A2 | 11/2010 |
| WO | WO-2011/025982 A2 | 3/2011 |
| WO | WO-2011/123536 A1 | 10/2011 |
| WO | WO-2012/021712 A1 | 2/2012 |
| WO | WO-2012/047907 A1 | 4/2012 |
| WO | WO-2014/036502 A2 | 3/2014 |
| WO | WO-2016/065290 A1 | 4/2016 |
| WO | WO-2017/097891 A1 | 6/2017 |
| WO | WO-2017/125557 A1 | 7/2017 |
| WO | WO-2018/045084 A1 | 3/2018 |
| WO | WO-2018/075767 A1 | 4/2018 |

OTHER PUBLICATIONS

Abbanat et al., "New agents in development for the treatment of bacterial infections," Curr Opin Pharmacol, 8(5):582-592 (2008).

Bhattacharyya et al., "Studies on Hydrofluorene Derivatives. Part II. Synthesis of 1,1a,1b,2,3,4,4a,5,6,6a-Decahydro-1a-methyl-3-oxochrysofluorene," Journal of the Indian Chemical Society, 41(7): 479-495 (1964).

Blackwood et al., "Some Transformations of Tetracycline at the 4-Position," Can J Chem, 43(5): 1382-1388 (1965).

Bocker, "Analysis and Quantitation of a Metabolite of Doxycycline in Mice, Rats, and Humans by High-Performance Liquid Chromatography," J Chromatogr-Biomed, 274: 255-262 (1983).

Bronson et al., "Quinolone, Everninomycin, Glycylcycline, Carbapenem, Lipopeptide and Cephem Antibacterials in Clinical Development," Curr Med Chem, 8: 1775-1793 (2001).

Charest et al., "A Convergent Enantioselective Route to Structurally Diverse 6-Deoxytetracycline Antibiotics", Science, 308:395-398 (2005).

(56) References Cited

OTHER PUBLICATIONS

Chen et al., "Oxidative Degradation Kinetics and Products of Chlortetracycline by Manganese Dioxide," J Hazard Mater, 193: 128-138 (2011).
Chopra et al., "Tetracycline Antibiotics: Mode of Action, Applications, Molecular Biology, and Epidemiology of Bacterial Resistance," Microbiol Mol Biol Rev, 65(2):232-260 (2001).
Ciara, "Crystalline Polymorphism of Organic Compounds," Topics in Current Chemistry, In: Weber E. et al. (eds) Design of Organic Solids. Topics in Current Chemistry, vol. 198. Springer, Berlin, Heidelberg 163-208 (1998).
Croisy-Delcey et al., "Synthesis of 1-Functionalized-6-hydroxy-4-methyl and 6,11-Dihydroxy-4-methylnaphtho[2,3-g]isoquinoline-5,12-quinoes," J. Heterocyclic Chem., 28:65-71 (1991).
Esse et al., "Tetracycloxides. II. Transformations at the C-4 Position", J Am Chem Soc, 86(18): 3875-3877 (1964).
Examination Report for New Zealand Patent Application No. 705849, dated Aug. 7, 2017.
Extended European Search Report for EP Application No. 17183980.6 dated Dec. 8, 2017.
Extended European Search Report for EP Application No. 18192684.1 dated Jan. 21, 2019.
Extended Search Report for European Patent Application No. 13172357.9 dated May 16, 2014 "C7-Fluoro Substituted Tetracycline Compounds".
HCAPLUS, Accession No. 2004:1036703, Document No. 141:420412 (Apr. 24, 2002).
HCAPLUS, Accession No. 2005:99455, Document No. 142:197754 (Jun. 25, 2004).
Hlavka et al., "The 6-Deoxytetracyclines. III. Electrophilic and Nucleophilic Substitution," Organic Chemical Research Section, Lederls Laboratories, (5 pages) (1961).
Hlavka et al., "The 6-Deoxytetracyclines. IV. A Photochemical Displacement of a Diazonium Group," J Org Chem, 27:3674-3675 (1962).
International Preliminary Report on Patentability for International Application No. PCT/US2010/001350; dated Nov. 9, 2011.
International Preliminary Report on Patentability for International Application No. PCT/US2010/047035; dated Feb. 28, 2012.
International Preliminary Report on Patentability for International Application No. PCT/US2011/047428; dated Feb. 12, 2013.
International Preliminary Report on Patentability for International Application No. PCT/US2013/057690, "Tetracycline Compounds", dated Mar. 3, 2015.
International Preliminary Report on Patentability for International Patent Application No. PCT/US2010/034718 dated Nov. 15, 2011.
International Preliminary Report on Patentability for International Patent Application No. PCT/US2011/030532 dated Oct. 2, 2012.
International Search Report and Written Opinion for International Application No. PCT/US2009/053142 dated Oct. 13, 2009.
International Search Report and Written Opinion for International Application No. PCT/US2017/049462 dated Feb. 14, 2018.
International Search Report and Written Opinion for International Application No. PCT/US2017/057385 dated Dec. 6, 2017.
International Search Report and Written Opinion for International Patent Application No. PCT/US2010/034718 dated Nov. 9, 2010.
International Search Report and Written Opinion for International Patent Application No. PCT/US2011/030532 dated Jul. 12, 2011.
International Search Report and Written Opinion of the International Searching Authority for International Application No. PCT/US2010/001348, dated Jul. 19, 2010.
International Search Report and Written Opinion of the International Searching Authority for International Application No. PCT/US2010/001350, dated Nov. 23, 2010.
International Search Report and Written Opinion of the International Searching Authority for International Application No. PCT/US2010/047035; dated Jul. 22, 2011.
International Search Report and Written Opinion of the International Searching Authority for International Application No. PCT/US2011/047428, dated Jan. 6, 2012.
International Search Report and Written Opinion of the International Searching Authority for International Application No. PCT/US2013/057690; dated Feb. 24, 2014.
International Search Report and Written Opinion of the International Searching Authority for International Application No. PCT/US2009/053142; dated Oct. 13, 2009.
Martin et al., "Totalsynthese von d,1-7-Chlor-6-desoxytetracyclinen und d,1-7-Chlor-6-desmethyl-6-desoxytetracyclinen der naturlichen, der 5a-epi- und der 6-epi-Reihe," Tetrahedron Letts 36:3513-3516 (1973).
Nelis et al., "Metabolism of Minocycline in Humans," Drug Metab Dispos, 10(2): 142-146 (1982).
Partial Translation of Hirayama, Yuki Kagoubutsu Kessho Sakusei Handobukku—Genri to Nouhau (Handbook for Preparing Organic Compound Crystals—Principles and Know-How), Maruzen Publishing Co (57-84) (2008).
Partial Translation of Takata et al., "API form screening and selection in drug discovery stage," Pharm Stage, 6(10): 20-25 (2007).
Plakunov, "Relation Between Chemical Structure of Tetracyclines and Their Analogs and Specific Features of Transport and Mechanism of Antibacterial Effect," Antibiotiki (Moscow), 18(12): 1069-1073 (1973).
Podlogar et al., "Patents on tetracycline and tetracycline derivatives as antimicrobials", Expert Opin. Ther. Patents, 13(4):467-478 (2003).
Pre-appeal Conference Decision dated Feb. 19, 2013 for U.S. Appl. No. 12/462,795.
Remmers et al., "New Alkaline-Stable Species for Selected Members of the Tetracycline Family," J Pharm Sci, 51(1): 86-87 (1962).
Rogalski, "Chemical Modifications of Tetracyclines," in Hlavka et al., The Tetracyclines. Handbook of Experimental Pharmacology (Continuation of Handbuch der experimentellen Pharmakologie), vol. 78.,Berlin, Spring-Verlag, pp. 179-316 (1985).
Ronn et al., "Process R&D of Eravacycline: The First Fully Synthetic Fluorocycline in Clinical Development," Organic Process Research and Development, 17(5): 838-845 (2013).
Sato et al. "Structure-Activity Relationship Investigation of Some New Tetracyclines by Electronic Index Methodology", arXiv:0708.2931 [q-bio.BM] 1-18 (2007).
Song et al., "Cytotoxic Effects of Tetracycline Analogues (Doxycycline, Minocycline and COL-3) in Acute Myeloid Leukemia HL-60 Cells," PLOS One, 9(12): e114457 (2014).
Sum et al., "Glycylcyclines. 1. A New Generation of Potent Antibacterial Agents Through Modification of 9-Aminotetracyclines," J Med Chem, 37: 184-188 (1994).
Sum et al., "Synthesis and Structure-Activity Relationship of Novel Glycylcycline Derivatives Leading to the Discovery of GAR-936," Bioorg Med Chem Letts 9:1459-1462 (1999).
Sun et al., "A Robust Platform for the Synthesis of New Tetracycline Antibiotics," J. Am. Chem.Soc., 130:17913-17927 (2008).
Sun et al., "Synthesis and Antibacterial Activity of Pentacyclines: A Novel Class of Tetracycline Analogs," J. Med. Chem. 54(11):3704-3731 (2011).
Van den Bogert et al., "Doxycycline in Combination Chemotherapy of a Rat Leukemia1," Cancer Research, 48: 6686-6690 (1988).
Verma et al., "Antibiotic and non-antibiotic tetracycline patents: 2002-2007", Expert Opin. Ther. Patents, vol. 18, pp. 69-82 (2008).
Zhang et al., "Process Development and Scale-up of Fully Synthetic Tetracyline TP-2758: A Potent Antibacterial Agent with Excellent Oral Bioavailabity," Org. Process Res. Dev., 20(2): 284-296 (2016).
Zurhelle et al., "Automated Residue Analysis of Tetracyclines and Their Metabolites in Whole Egg, Egg White, Egg Yolk and Hen's Plasma Utilizing a Modified ASTED System," Journal of Chromatography B: Biomedical Sciences and Applications, 739(1): 191-203 (2000).

CRYSTALLINE FORMS OF ERAVACYCLINE

RELATED APPLICATION

This application is a continuation of U.S. application Ser. No. 16/342,779, filed on Apr. 17, 2019, which is the U.S. National Stage of International Application No. PCT/US2017/57385, filed on Oct. 19, 2017, published in English, which claims the benefit of U.S. Provisional Application No. 62/410,230, filed on Oct. 19, 2016. The entire teachings of the above application is incorporated herein by reference.

GOVERNMENT SUPPORT

This invention was made with government support under Contract No. HHSO100201200002C and Subcontract No. 7834S1 awarded by the Department of Health and Human Services. The government has certain rights in the invention.

BACKGROUND OF THE INVENTION

The tetracyclines are broad spectrum anti-microbial agents that are widely used in human and veterinary medicine. The total production of tetracyclines by fermentation or semi-synthesis is measured in the thousands of metric tons per year.

The widespread use of tetracyclines for therapeutic purposes has led to the emergence of resistance to these antibiotics, even among highly susceptible bacterial species. Tetracycline analogs having improved antibacterial activities and efficacies against other tetracycline responsive diseases or disorders have been described (see, for example, U.S. Pat. No. 8,796,245). A particularly potent compound is eravacycline (7-fluoro-9-pyrrolidinoacetamido-6-demethyl-6-deoxytetracycline), which has the chemical structure shown in Structural Formula 1:

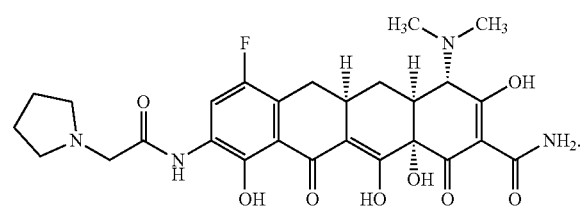

(1)

The solid form of a compound can be important in the formulation of pharmaceutical compositions. For example, crystalline and amorphous forms of a compound can have different physical properties (e.g., stability, dissolution rate, density, etc.) relating to their suitability for use in pharmaceutical compositions. The difference in physical properties can also affect a crystalline or amorphous form's usefulness, for example, as an intermediate in the synthesis of a form suitable for use in pharmaceutical compositions.

There is a need for crystalline forms of eravacycline that are thermodynamically stable and suitable for use in pharmaceutical compositions (e.g., are readily dissolvable, exhibit good flow properties and/or good chemical stability). There is a further need for crystalline forms of eravacycline having physical properties that enable the manufacture of eravacycline for use in pharmaceutical compositions in high yield and high purity.

SUMMARY OF THE INVENTION

The present invention relates to crystalline forms of the bis HCl salt of the compound represented by Structural Formula 1, designated crystalline Form A, crystalline Form B, crystalline Form I and crystalline Form J and compositions comprising the crystalline forms.

In one embodiment, a crystalline form of a compound represented by the bis HCl salt of Structural Formula 1 is provided, wherein the crystalline form is Form I. In this embodiment, crystalline Form I is characterized by at least three x-ray powder diffraction peaks at 2θ angles selected from 7.22°, 7.80°, 10.41°, and 11.11°.

In another embodiment, a crystalline form of a compound represented by bis HCl salt of Structural Formula 1 is provided, wherein the crystalline form is Form J. In this embodiment, crystalline Form J is characterized by at least three x-ray powder diffraction peaks at 2θ angles selected from 7.02°, 7.80°, 22.13°, and 23.22°.

In yet another embodiment, a crystalline form of a compound represented by the bis HCl salt of Structural Formula 1 is provided, wherein the crystalline form is Form A. In this embodiment, crystalline Form A is characterized by at least three x-ray powder diffraction peaks at 2θ angles selected from 3.31°, 6.01°, 6.33°, and 8.73°.

In another embodiment, a crystalline form of a compound represented by the bis HCl salt of Structural Formula 1 is provided, wherein the crystalline form is Form B. In this embodiment, crystalline Form B is characterized by at least three x-ray powder diffraction peaks at 2θ angles selected from 9.19°, 9.66°, 23.32°, and 24.35°.

Another embodiment, is a composition comprising particles of one or more crystalline forms of a compound represented by the bis HCl salt of Structural Formula 1:

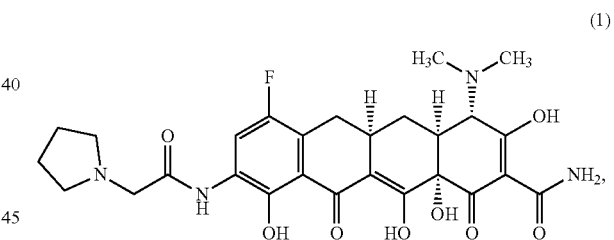

(1)

wherein the particles are selected from: particles of crystalline Form I characterized by at least three x-ray powder diffraction peaks at 2θ angles selected from 7.22°, 7.80°, 10.41°, and 11.11°; particles of crystalline form Form J characterized by at least three x-ray powder diffraction peaks at 2θ angles selected from 7.02°, 7.80°, 22.13°, and 23.22°; particles of crystalline Form A characterized by at least three x-ray powder diffraction peaks at 2θ angles selected from 3.31°, 6.01°, 6.33°, and 8.73°; and particles of crystalline Form B characterized by at least three x-ray powder diffraction peaks at 2θ angles selected from 9.19°, 9.66°, 23.32°, and 24.35°. In a specific aspect, the composition comprises particles of crystalline Form I and crystalline form J. In another aspect, the weight percent of crystalline Form J in the composition is 25% or less (e.g., about 20% or less, about 15% or less, about 10% or less, about 5% or less or about 1%).

Another embodiment is a pharmaceutical composition comprising particles of Form I, Form J, Form A, Form B or mixtures thereof and a pharmaceutically acceptable carrier.

A further embodiment is a method for treating or preventing a tetracycline-responsive disease or disorder, the method comprising administering to a subject in need thereof a therapeutically or prophylactically effective amount of crystalline Form I, Form J, Form A, Form B or a mixture thereof. In one aspect, the tetracycline-responsive disease or disorder is an infection. In a specific aspect, the infection is caused by bacteria.

BRIEF DESCRIPTION OF THE DRAWINGS

The foregoing will be apparent from the following more particular description of example embodiments of the invention.

DETAILED DESCRIPTION OF THE INVENTION

Figure 1:
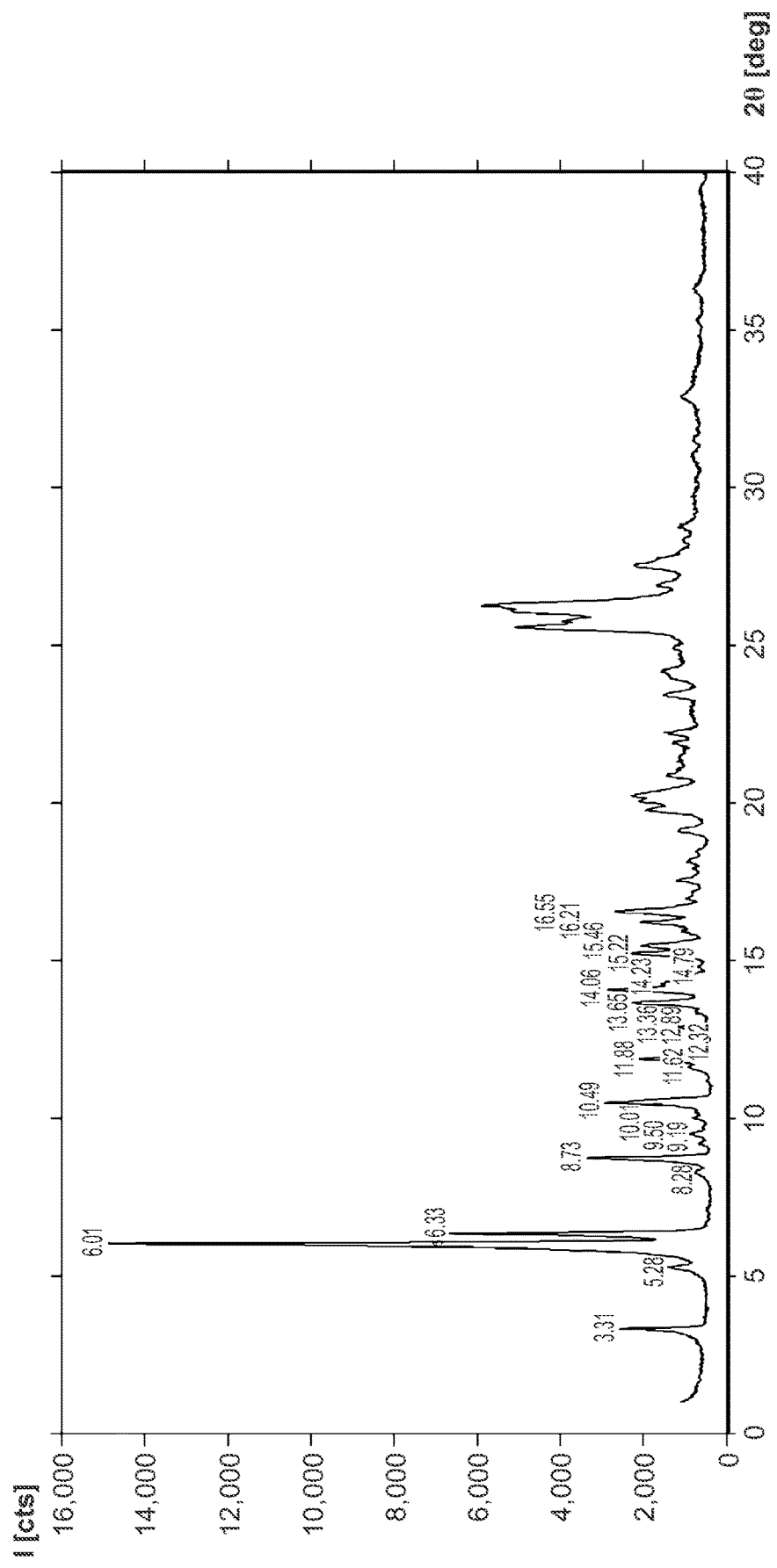
FIG. 1 is an x-ray powder diffraction (XRPD) pattern of Structural Formula 1 as the bis HCl salt)—Form A.

A description of example embodiments of the invention follows.

Crystalline Forms of Eravacycline

Provided herein are crystalline forms of the bis HCl salt of the compound represented by Structural Formula 1, designated crystalline Form A, crystalline Form B, crystalline Form I and crystalline Form J.

"Crystalline," as used herein, refers to a homogeneous solid formed by a repeating, three-dimensional pattern of atoms, ions or molecules (e.g., an anhydrous molecule or a salt thereof, solvate thereof, or combination of the foregoing) having fixed distances between constituent parts. The unit cell is the simplest repeating unit in this pattern.

A crystalline form provided herein can be a single crystalline form or can comprise a mixture of two or more different crystalline forms. For example, in some embodiments, crystalline Forms A, B, I, and J of a compound of Structural Formula 1 are provided as single crystalline forms (i.e., single crystalline Form A, single crystalline Form B, single crystalline Form I, single crystalline Form J). Alternatively, a crystalline form can comprise a mixture of two or more crystalline forms of a compound of Structural Formula 1 (e.g., a mixture of two or more of crystalline Forms A, B, I, and J, specifically, of crystalline Forms I and J).

"Single crystalline form," as used herein, refers to a single crystal of a crystalline solid or a plurality of crystals of a crystalline solid wherein each of the plurality of crystals has the same crystal form.

The crystalline forms provided herein can be identified on the basis of characteristic peaks in an x-ray powder diffraction (XRPD) analysis. XRPD is a scientific technique that measures the x-rays, neutrons or electrons scattered by a powder or microcrystalline material as a function of scattering angle. XRPD can be used to identify and characterize crystalline solids, as the diffraction pattern produced by a particular solid is typically distinctive to that solid and can be used as a "fingerprint" to identify that solid. For example, an XRPD pattern or diffractogram (e.g., a pattern or diffractogram produced by a sample, such as an unknown sample) that is substantially in accordance with a reference XRPD pattern or diffractogram can be used to determine the identity between the sample material and the reference material. Both the position and the relative intensity of the peaks in an XRPD diffractogram are indicative of the particular phase and identity of a material.

FIGS. 1, 3, 5, and 7 show XRPD patterns of various crystalline forms described herein. An XRPD pattern that is "substantially in accordance" with one or more figures herein showing an XRPD pattern or diffractogram is an XRPD pattern that would be considered by one skilled in the art to represent the same crystalline form of the compound of Structural Formula 1 as the sample of the compound of Structural Formula 1 that provided the XRPD pattern of one or more figures provided herein. Thus, an XRPD pattern that is substantially in accordance may be identical to that of one of the figures or, more likely, may be somewhat different from one or more of the figures. An XRPD pattern that is somewhat different from one or more of the figures may not necessarily show each of the lines of the diffraction pattern presented herein and/or may show a slight change in appearance or intensity of the lines or a shift in the position of the lines. These differences typically result from differences in the conditions involved in obtaining the data or differences in the purity of the sample used to obtain the data. A person skilled in the art is capable of determining if a sample of a crystalline compound is of the same form as or a different form from a form disclosed herein by comparison of the XRPD pattern of the sample and the corresponding XRPD pattern disclosed herein.

It is to be understood that any 2θ angle specified herein means the specified value±0.2°. For example, when a described embodiment or a claim specifies a 2θ of 4.4°, this is to be understood to mean 4.4°±0.2°, that is, a 2θ angle of from 4.2° to 4.6°.

The crystalline forms provided herein can also be identified on the basis of differential scanning calorimetry (DSC) and/or thermogravimetric analysis (TGA). DSC is a thermoanalytical technique in which the difference in the amount of heat required to increase the temperature of a sample is measured as a function of temperature. DSC can be used to detect physical transformations, such as phase transitions, of a sample. For example, DSC can be used to detect the temperature(s) at which a sample undergoes crystallization, melting or glass transition.

TGA is a method of thermal gravimetric analysis in which changes in physical and chemical properties of a material are measured as a function of increasing temperature (with constant heating rate) or as a function of time (with constant temperature and/or constant mass loss). TGA can provide information about physical phenomena, such as second-order phase transitions, or about chemical phenomena, such as desolvation and/or decomposition.

FIGS. 2B, 4B, 6B and 8B show DSC thermograms of various crystalline forms described herein. FIGS. 2A, 4A, 6A, and 8A show TGA thermograms of various crystalline forms described herein. A DSC or TGA thermogram that is "substantially in accordance" with one or more figures herein showing a DSC or TGA thermogram is a DSC or TGA thermogram that would be considered by one skilled in the art to represent the same crystalline form of the compound of Structural Formula 1 as the sample of the compound of Structural Formula 1 that provided the DSC or TGA thermogram of one or more figures provided herein.

It is to be understood that any temperature associated with DSC or TGA specified herein means the specified value±5° C. or less. For example, when an embodiment or a claim specifies an endothermic peak at about 179° C., this is to be understood to mean 179° C.±5° C. or less, that is a temperature of from 174° C. to 184° C. In preferred embodiments, a DSC or TGA temperature is the specified value±3° C., in more preferred embodiments, ±2° C.

In some embodiments, crystalline forms are solvates. "Solvate," as used herein, refers to a chemical compound formed by the interaction of a solute (e.g., a compound of Structural Formula 1) and one or more solvents (e.g., methanol, ethanol, water). Thus, "solvate" includes solvates containing a single type of solvent molecule and solvates containing more than one type of solvent molecule (mixed solvates or co-solvates). Typically, the one or more solvents in solvates described herein is an organic solvent or a combination of organic solvents, although water can also form solvates, called hydrates.

For example, Form I described herein has been characterized as a hemi-ethanolate with 0.5 eq. of ethanol. Form J described herein has been characterized as the desolvated Form of I.

Form I:

In a first embodiment, a crystalline form of a compound represented by the bis HCl salt of Structural Formula 1 is provided, wherein the crystalline form is Form I and is characterized by at least three x-ray powder diffraction peaks at 2θ angles selected from 7.22°, 7.80°, 10.41°, and 11.11°, or at least four x-ray powder diffraction peaks at 2θ angles selected from 7.22°, 7.80°, 8.19°, 10.41°, and 11.11°, at least five x-ray powder diffraction peaks at 2θ angles selected from 7.22°, 7.80°, 8.19°, 10.41°, 11.11°, 15.00°, 16.47° and 20.44°. In a particular embodiment, Form I is characterized by x-ray powder diffraction peaks at 2θ angles of 7.22°, 7.80°, 10.41°, and 11.11°, or by x-ray powder diffraction peaks at 2θ angles of 7.22°, 7.80°, 8.19°, 10.41°, and 11.11°, or by x-ray powder diffraction peaks at 2θ angles of 7.22°, 7.80°, 8.19°, 10.41°, 11.11°, 15.00°, 16.47° and 20.44° or by x-ray powder diffraction peaks at 2θ angles of 7.22°, 7.80°, 8.19°, 10.41°, 11.11°, 12.17°, 13.52°, 15.00°, 15.70°, 16.47°, 19.96°, and 20.44°. In some embodiments, crystalline Form I is characterized by an x-ray powder diffraction pattern substantially in accordance with that depicted in FIG. 5.

Crystalline Form I may be further characterized by a differential scanning calorimetry thermogram comprising a broad, weak endothermic peak at about 116° C. or a weak endothermic peak at about 171° C. In some embodiments, the TGA thermogram and/or the DSC thermogram are substantially in accordance with those in FIG. 6A or FIG. 6B.

In a particular embodiment, Form I is in the form of a solvate, for example, an ethanol solvate, such as a hemi-ethanolate comprising about 0.5 molar equivalents of solute per molar equivalent of the compound of Structural Formula 1.

In another embodiment, Form I is in the form of a co-solvate. In a particular embodiment, the co-solvate is a dihydrate and hemi-ethanol co-solvate.

Form J:

In a second embodiment, a crystalline form of a compound represented by bis HCl salt of Structural Formula 1 is provided, wherein the crystalline form is Form J and is characterized by at least three x-ray powder diffraction peaks at 2θ angles selected from 7.02°, 7.80°, 22.13°, and 23.22°, at least four x-ray powder diffraction peaks at 2θ angles selected from 7.02°, 7.80°, 10.25°, 22.13°, and 23.22°, or at least five x-ray powder diffraction peaks at 2θ angles selected from 7.02°, 7.80°, 10.25°, 11.00°, 13.29°, 13.60°, 14.98°, 21.92°, 22.13°, 23.22°, 24.02° and 25.28°.

In a particular embodiment, Form J is characterized by x-ray powder diffraction peaks at 2θ angles of 7.02°, 7.80°, 22.13°, and 23.22°, or by x-ray powder diffraction peaks at 2θ angles of 7.02°, 7.80°, 10.25°, 22.13°, and 23.22° or by x-ray powder diffraction peaks at 2θ angles of 7.02°, 7.80°, 10.25°, 11.00°, 13.29°, 13.60°, 14.98°, 21.92°, 22.13°, 23.22°, 24.02° and 25.28°. In another particular embodiment, Form J is characterized by x-ray powder diffraction peaks at 2θ angles of 7.02°, 7.80°, 10.25°, 11.00°, 11.85°, 13.29°, 13.60°, 14.98°, 15.27°, 16.21°, 16.39°, 17.04°, 20.10°, 21.53°, 21.92°, 22.13°, 22.52°, 23.22°, 24.02°, 24.41°, 25.28°, 26.08°, 26.35°, 26.78°, and 27.90°. In some embodiments, crystalline Form J is characterized by an x-ray powder diffraction pattern substantially in accordance with that depicted in FIG. 7.

Crystalline Form J may be further characterized by a differential scanning calorimetry thermogram comprising a broad endothermic peak at 118° C. In some embodiments, the TGA thermogram and/or the DSC thermogram are substantially in accordance with those in FIG. 8A or FIG. 8B.

Form A:

In a third embodiment, a crystalline form of a compound represented by the bis HCl salt of Structural Formula 1 is provided, wherein the crystalline form is Form A and is characterized by at least three x-ray powder diffraction peaks at 2θ angles selected from 3.31°, 6.01°, 6.33°, and 8.73°, at least four x-ray powder diffraction peaks at 2θ angles selected from 3.31°, 6.01°, 6.33°, 8.73°, and 14.06°, or at least five x-ray powder diffraction peaks at 2θ angles selected from 3.31°, 6.01°, 6.33°, 8.73°, 10.49°, 14.06° and 16.55°. In a particular embodiment, Form A is characterized by x-ray powder diffraction peaks at 2θ angles of 3.31°, 6.01°, 6.33°, and 8.73°, or by x-ray powder diffraction peaks at 2θ angles of 3.31°, 6.01°, 6.33°, 8.73°, and 14.06°, or by x-ray powder diffraction peaks at 2θ angles of 3.31°, 6.01°, 6.33°, 8.73°, 10.49°, 14.06° and 16.55°, In some embodiments, crystalline Form A is characterized by an x-ray powder diffraction pattern substantially in accordance with that depicted in FIG. 1.

Crystalline Form A may be further characterized by a differential scanning calorimetry thermogram comprising a broad, endothermic peak at about 120° C. In some embodiments, the TGA thermogram and/or the DSC thermogram are substantially in accordance with those in FIG. 2A or FIG. 2B.

In a particular embodiment, Form A is in the form of a solvate or a co-solvate, for example, a water and ethanol co-solvate. In a particular embodiment, the water and ethanol co-solvate is a variable co-solvate.

Form B:

In a fourth embodiment, a crystalline form of a compound represented by the bis HCl salt Structural Formula 1 is provided, wherein the crystalline form is Form B and is characterized by at least three x-ray powder diffraction peaks at 2θ angles selected from 9.19°, 9.66°, 23.32°, and 24.35°, by at least four x-ray powder diffraction peaks at 2θ angles selected from 9.19°, 9.66°, 17.63°, 23.32°, and 24.35°, or by at least five x-ray powder diffraction peaks at 2θ angles selected from 6.10°, 9.19°, 9.48°, 9.66°, 13.05°, 17.63°, 17.77°, 19.94°, 20.48°, 23.32° and 24.35°. In a particular embodiment, Form B is characterized by x-ray powder diffraction peaks at 2θ angles of 9.19°, 9.66°, 23.32°, and 24.35°, or by x-ray powder diffraction peaks at 2θ angles of 9.19°, 9.66°, 17.63°, 23.32°, and 24.35°, or by x-ray powder diffraction peaks at 2θ angles of 6.10°, 9.19°, 9.48°, 9.66°, 13.05°, 17.63°, 17.77°, 19.94°, 20.48°, 23.32°, 23.87°, and 24.35°, or by x-ray powder diffraction peaks at 2θ angles of 6.10°, 9.19°, 9.48°, 9.66°, 12.08°, 13.05°, 17.63°, 17.77°, 19.54°, 19.94°, 20.48°, 23.32°, 23.87°, and 24.35°. In some embodiments, crystalline Form B is characterized by an x-ray powder diffraction pattern substantially in accordance with that depicted in any of FIG. 3.

Figure 4A:
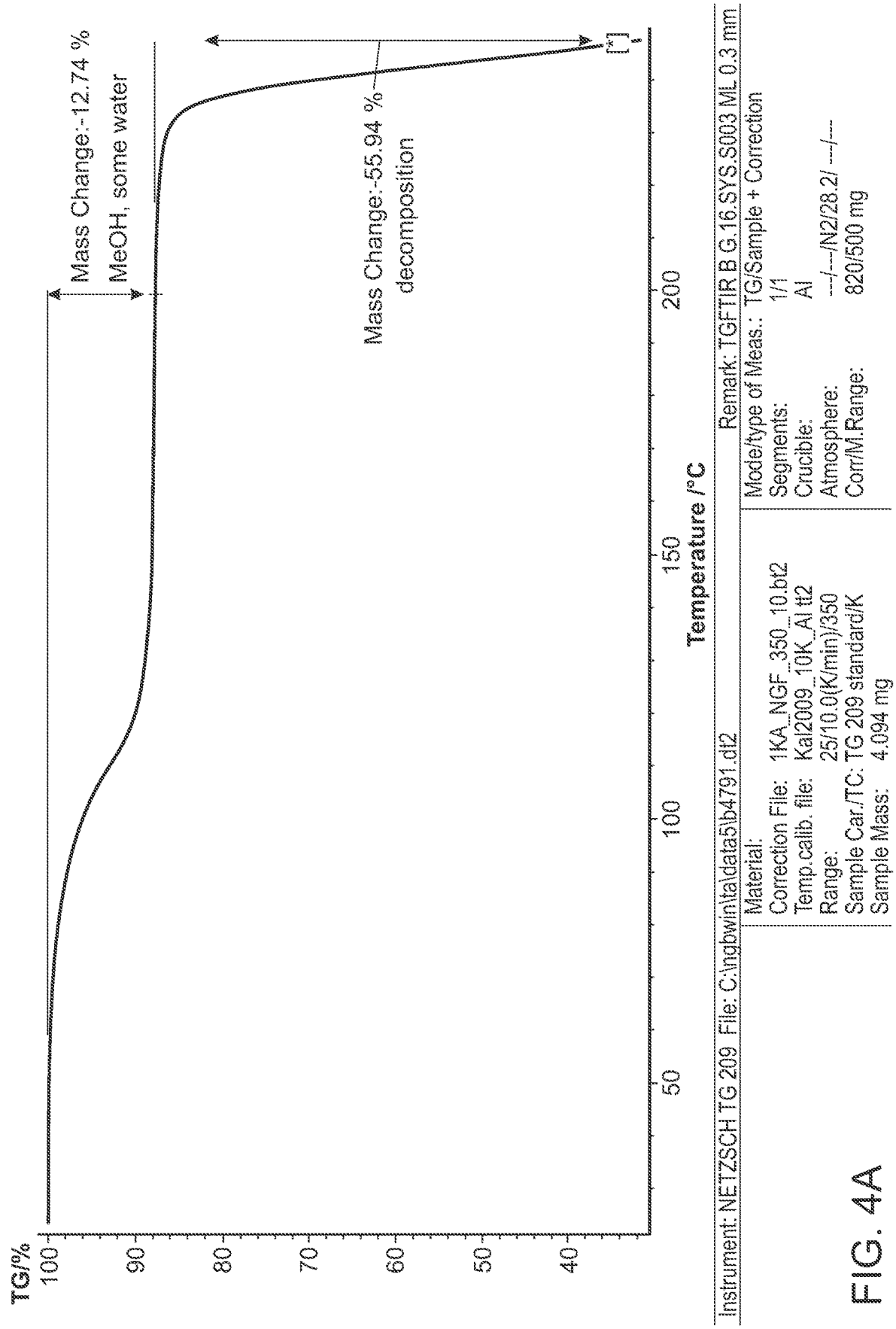
FIG. 4A is a TGA thermogram of Structural Formula 1—Form B.
Figure 4B:
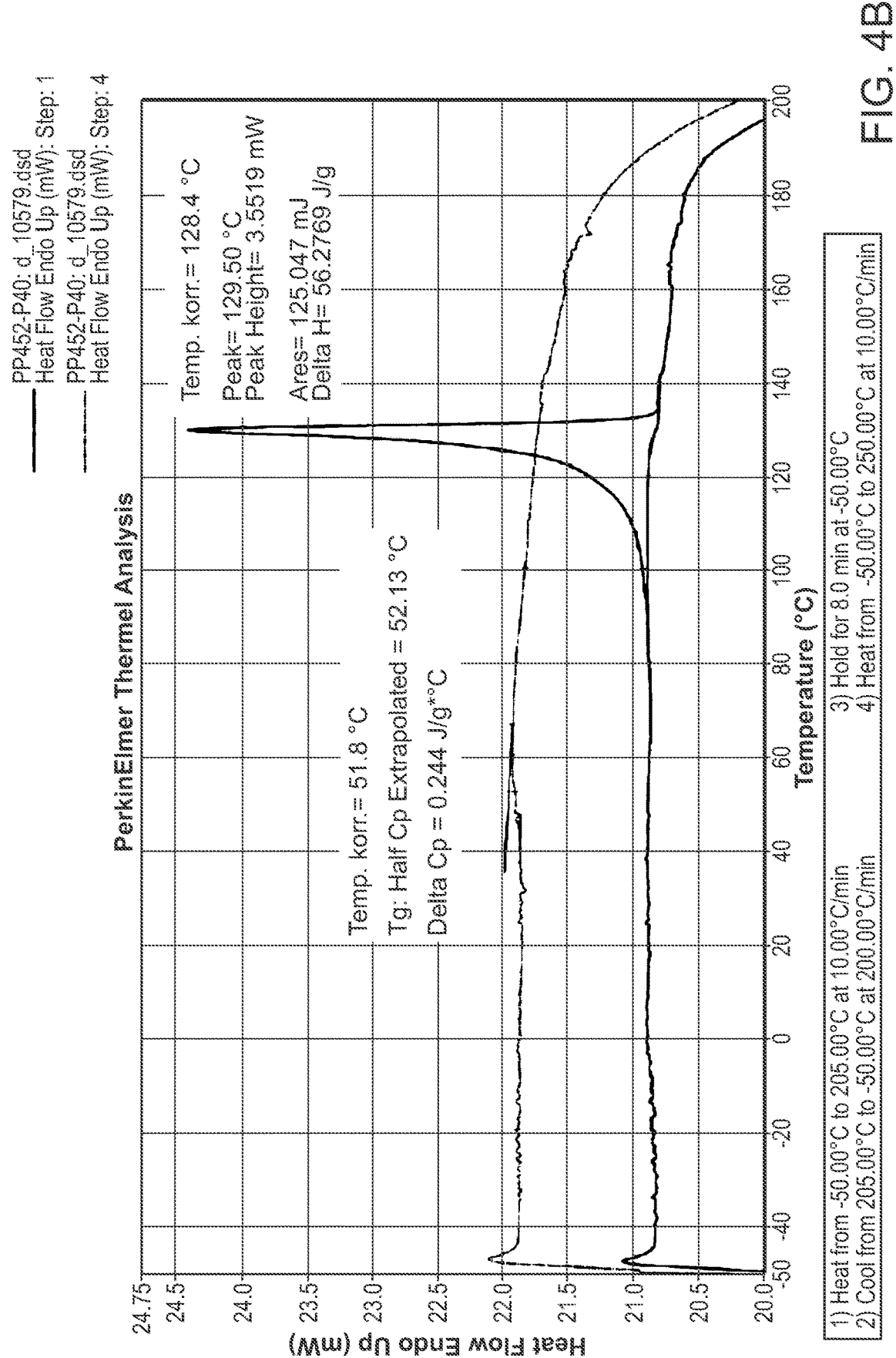
FIG. 4B is a DSC thermogram of Structural Formula 1—Form B.

Crystalline Form B may be further characterized by a differential scanning calorimetry thermogram of FIG. 4B and a melting peak of 128° C. In some embodiments, the TGA thermogram and/or the DSC thermogram are substantially in accordance with those in FIG. 4A or FIG. 4B.

In a particular embodiment, Form B is in the form of a solvate or a co-solvate, for example, a water and methanol co-solvate.

Crystalline Form B can be prepared, in accordance with the methods disclosed herein, at a desirable purity and yield. The exceptional purity of crystalline Form B can be translated into highly pure crystalline Form I, crystalline Form J or a mixture of crystalline Forms I and J for pharmaceutical use. By using the procedures described herein for converting crystalline Form B into crystalline Forms I, crystalline Form J or a mixture thereof, crystalline Form I, crystalline Form J or a mixture thereof can be isolated as a composition ready for formulation as a pharmaceutical composition (e.g., acceptable purity, readily dissolvable and/or exhibiting good flow properties).

Compositions and Pharmaceutical Compositions

In another embodiment, the invention relates to a composition, comprising particles of one or more crystalline forms of a compound represented by the bis HCl salt of Structural Formula 1:

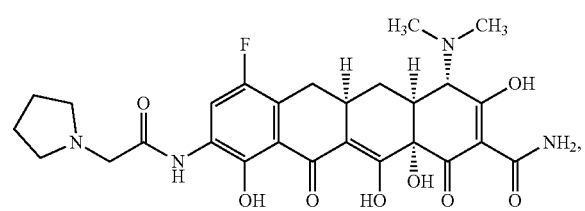

(1)

wherein, the one or more crystalline forms are selected from:
crystalline Form I characterized by at least three x-ray powder diffraction peaks at 2θ angles selected from 7.22°, 7.80°, 10.41°, and 11.11';
crystalline form Form J characterized by at least three x-ray powder diffraction peaks at 2θ angles selected from 7.02°, 7.80°, 22.13°, and 23.22°;
crystalline Form A characterized by at least three x-ray powder diffraction peaks at 2θ angles selected from 3.31°, 6.01°, 6.33°, and 8.73°; and
crystalline Form B characterized by at least three x-ray powder diffraction peaks at 2θ angles selected from 9.19°, 9.66°, 23.32°, and 24.35°.

In a particular embodiment, the composition comprises particles that are a mixture of crystalline Form I and crystalline Form J. In one aspect, the weight percent of crystalline Form J in the composition is 25% or less (e.g., about 20% or less, about 15% or less, about 10% or less, about 5% or less or about 1%.

Also provided herein are pharmaceutical compositions comprising a crystalline form (e.g., Form A, B, I, or J) of compositions described herein and a pharmaceutically acceptable carrier. The composition comprises particles of one or more crystalline form (e.g., Form A, B, I, or J) of the bis HCl salt of a compound of Structural Formula 1. For example, the pharmaceutical composition comprises Form I, Form J, Form A, Form B or a combination of more than one of Form I, Form J, Form A and Form B. In a particular embodiment, the pharmaceutical composition comprises a mixture of Form I and Form J.

In certain embodiments, the invention relates to the compositions and pharmaceutical compositions as described herein, wherein the crystalline form is characterized by at least three x-ray powder diffraction peaks at 2θ angles selected from 7.22°, 7.80°, 10.41°, and 11.11°, at least four x-ray powder diffraction peaks at 2θ angles selected from 7.22°, 7.80°, 8.19°, 10.41°, and 11.11°, or at least five x-ray powder diffraction peaks at 2θ angles selected from 7.22°, 7.80°, 8.19°, 10.41°, 11.11°, 15.00°, 16.47° and 20.44°.

In certain embodiments, the invention relates to compositions and pharmaceutical compositions described herein, wherein the crystalline form is characterized by x-ray powder diffraction peaks at 2θ angles of 7.22°, 7.80°, 10.41°, and 11.11°, by x-ray powder diffraction peaks at 2θ angles of 7.22°, 7.80°, 8.19°, 10.41°, and 11.11°, or by x-ray powder diffraction peaks at 2θ angles of 7.22°, 7.80°, 8.19°, 10.41°, 11.11°, 15.00°, 16.47° and 20.44°.

Figure 5:
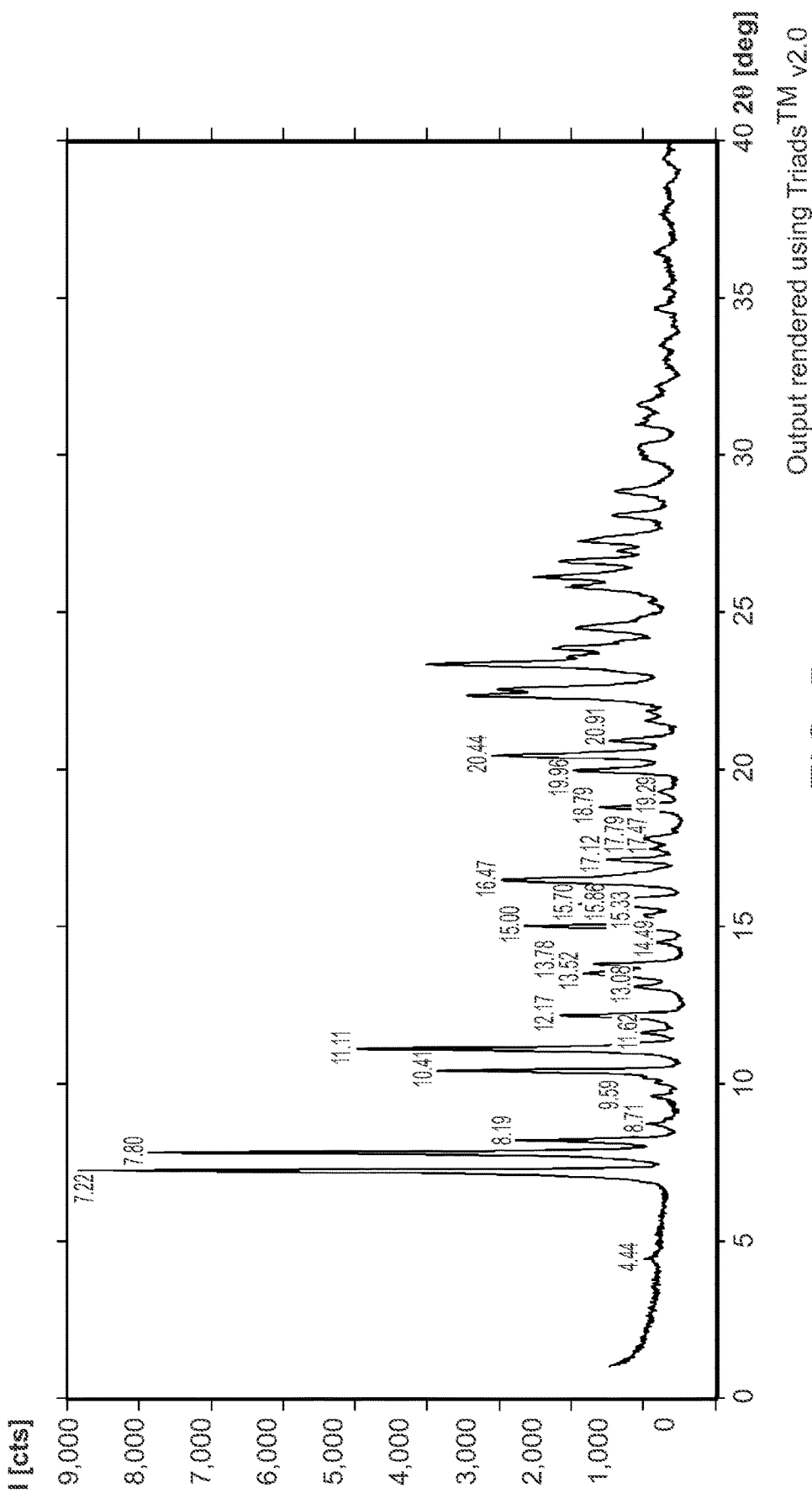
FIG. 5 is an XRPD pattern of Structural Formula 1—Form I.

In certain embodiments, the invention relates to compositions and pharmaceutical compositions described herein, wherein the crystalline form is characterized by an x-ray powder diffraction pattern substantially in accordance with that depicted in FIG. 5.

In certain embodiments, the invention relates to compositions and pharmaceutical compositions described herein, wherein the crystalline form is further characterized by a differential scanning calorimetry thermogram comprising a broad, weak endothermic peak at about 116° C. or a weak endothermic peak at about 171° C. In certain embodiments, the invention relates to any of the compositions described herein, wherein the crystalline form is further characterized by a differential scanning calorimetry thermogram comprising a broad, weak endothermic peak at about 116° C. In certain embodiments, the invention relates to any of the compositions described herein, wherein the crystalline form is further characterized by a differential scanning calorimetry thermogram comprising a weak endothermic peak at about 171° C.

In certain embodiments, the invention relates to the compositions and pharmaceutical compositions as described herein, wherein the crystalline form is characterized by at least three x-ray powder diffraction peaks at 2θ angles selected from 7.02°, 7.80°, 22.13°, and 23.22°, at least four x-ray powder diffraction peaks at 2θ angles selected from 7.02°, 7.80°, 10.25°, 22.13°, and 23.22°, or at least five x-ray powder diffraction peaks at 2θ angles selected from 7.02°, 7.80°, 10.25°, 11.00°, 13.29°, 13.60°, 14.98°, 21.92°, 22.13°, 23.22°, 24.02°, 25.28°.

In certain embodiments, the invention relates to any of the compositions described herein, wherein the crystalline form is characterized by x-ray powder diffraction peaks at 2θ angles of 7.02°, 7.80°, 22.13°, and 23.22°, or by x-ray powder diffraction peaks at 2θ angles of 7.02°, 7.80°, 10.25°, 22.13°, and 23.22, or by x-ray powder diffraction peaks at 2θ angles of 7.02°, 7.80°, 10.25°, 11.00°, 13.29°, 13.60°, 14.98°, 21.92°, 22.13°, 23.22°, 24.02° and 25.28° or by x-ray powder diffraction peaks at 2θ angles of 7.02°, 7.80°, 10.25°, 11.00°, 11.85°, 13.29°, 13.60°, 14.98°, 15.27°, 16.21°, 16.39°, 17.04°, 20.10°, 21.53°, 21.92°, 22.13°, 22.52°, 23.22°, 24.02°, 24.41°, 25.28°, 26.08°, 26.35°, 26.78°, and 27.90°.

Figure 7:
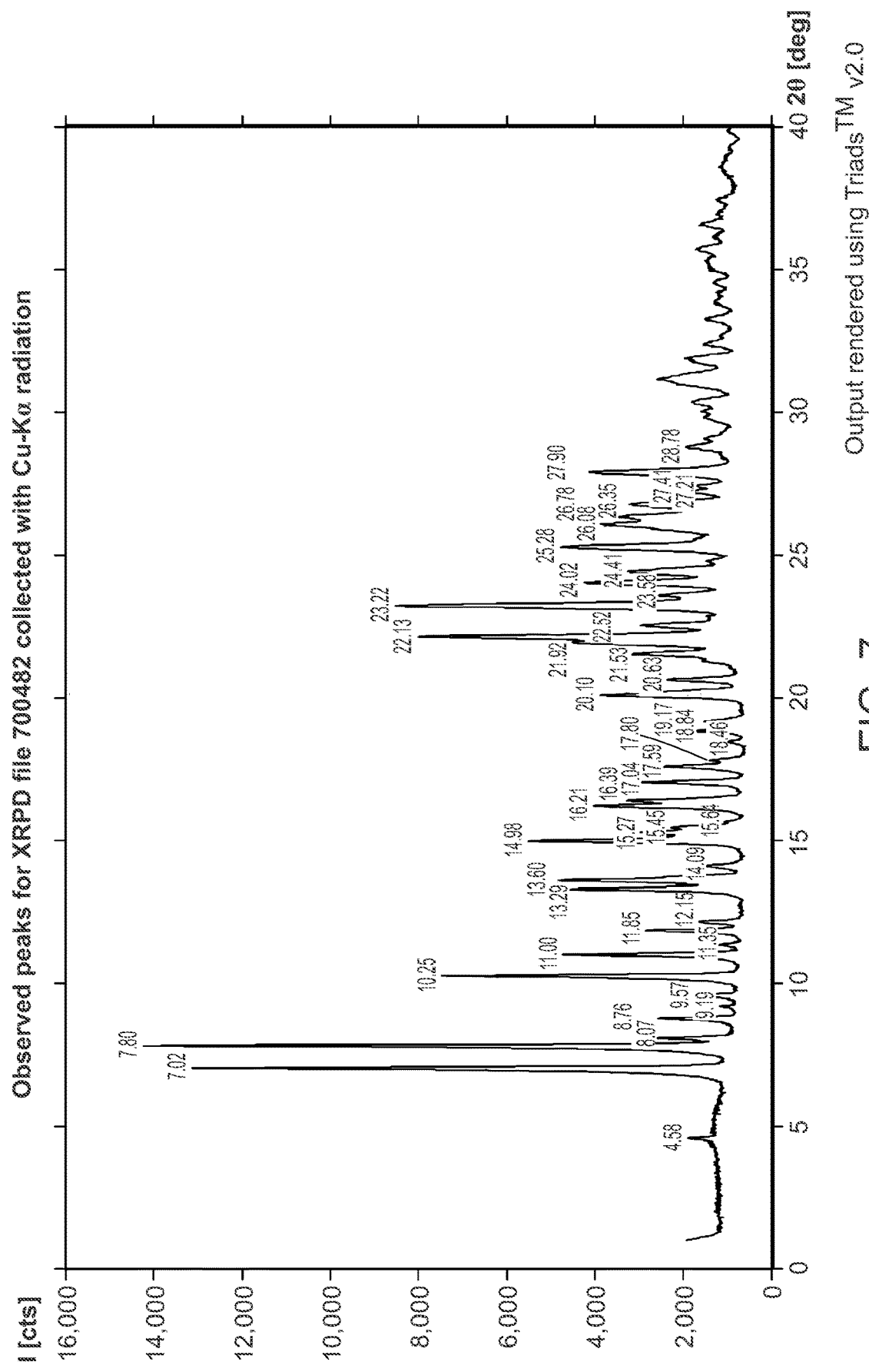
FIG. 7 is an XRPD pattern of Structural Formula 1—Form J.

In certain embodiments, the invention relates to compositions or pharmaceutical compositions described herein, wherein the crystalline form is characterized by an x-ray powder diffraction pattern substantially in accordance with that depicted in FIG. 7.

In certain embodiments, the invention relates to any of the compositions described herein, wherein the crystalline form is further characterized by a differential scanning calorimetry thermogram comprising a broad endothermic peak at 118° C.

In certain embodiments, the invention relates to any of the compositions described herein, wherein the crystalline form is characterized by an x-ray powder diffraction pattern having a widened shoulder on the peak at 7.2° 2θ as compared to the x-ray powder diffraction pattern of particles of Form I.

In certain embodiments, the invention relates to any of the compositions described herein, wherein the composition comprises a mixture of particles of Form I and particles of Form J; and the crystalline form is characterized by an x-ray powder diffraction pattern having a widened shoulder on the peak at 7.2° 2θ as compared to the x-ray powder diffraction pattern of particles of Form I.

The term "pharmaceutically acceptable carrier" means a non-toxic solvent, dispersant, excipient, adjuvant or other material which is mixed with the active ingredient in order to permit formation of a pharmaceutical composition, i.e., a dosage form capable of being administered to a subject. A "pharmaceutically acceptable carrier" should not destroy the activity of the compound with which it is formulated. Pharmaceutically acceptable carriers are well known in the art.

Pharmaceutically acceptable carriers, adjuvants or vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutical compositions of the invention may be administered orally, parenterally (including subcutaneous, intramuscular, intravenous and intradermal), by inhalation spray, topically, rectally, nasally, buccally, vaginally or via an implanted reservoir. In some embodiments, provided pharmaceutical compositions are administrable intravenously and/or intraperitoneally.

The term "parenteral" as used herein includes subcutaneous, intravenous, intramuscular, intraocular, intravitreal, intra-articular, intra-synovial, intrasternal, intrathecal, intrahepatic, intraperitoneal intralesional and intracranial injection or infusion techniques. Preferably, the pharmaceutical compositions are administered orally, subcutaneously, intraperitoneally or intravenously. Sterile injectable forms of the pharmaceutical compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Pharmaceutical compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In some embodiments, a provided oral formulation is formulated for immediate release or sustained/delayed release. In some embodiments, the composition is suitable for buccal or sublingual administration, including tablets, lozenges and pastilles. A provided compound can also be in micro-encapsulated form.

Specific pharmaceutically acceptable carriers suitable for use in an oral formulation such as a tablet or capsule include, but are not limited to, microcrystalline cellulose (Avicel PH101), croscarmellose Sodium (Ac-Di-Sol), kollidon 30 powder (polyvinylpyrrolidone, povidone), colloidal silicon dioxide M5-P, magnesium stearate, microcrystalline cellulose (Avcel PH102), sodium lauryl sulfate (Kolliphor SLS Fine) and Colloidal Silicon Dioxide M5-P. Each of the above listed carriers can be used in an oral formulation either alone or in any combination.

Further pharmaceutically acceptable carriers suitable for use in an oral formulation such as a tablet or capsule include, but are not limited to, microcrystalline cellulose (Avicel PH112), crospovidone (polyplasdone XL-10), colloidal silicone dioxide (Cab-O-Sil M-5P), Talc, starch and calcium stearate. In a particular aspect, the crystalline form (e.g., Form A, Form B, Form I, Form J or a mixture of Form I and Form J) is present in the oral formulation from about 25-45% by weight (freebase weight). In other aspects, Disodium EDTA is also present in the oral formulation. In certain aspects, the EDTA increases the bioavailability of the active. In a particular embodiment, the bioavailability of the active is increased by from about 1.5 fold to about 20 fold (e.g., 1.5, 2, 3, 4, 5, 6, 7, 8, 9, 10, 11, 12, 13, 14, 15, 16, 17, 18, 19 or 20 fold). When EDTA is present in the formulation, the w/w ratio of the crystalline form (freebase weight) to EDTA ranges from about 1:0.25 to about 1:15 (e.g., 1:0.25, 1:0.5, 1:1, 1:2.5, 1:5, 1:10, or 1:15). For ophthalmic use, provided pharmaceutical compositions may be formulated as micronized suspensions or in an ointment such as petrolatum.

Pharmaceutical compositions of this invention may also be administered by nasal aerosol or inhalation.

In some embodiments, pharmaceutical compositions of this invention are formulated for intra-peritoneal administration.

The amount of the crystalline form of a compound represented by the bis HCl salt Structural Formula 1 in pharmaceutical compositions of this invention is such that is effective to measurably treat or prevent a tetracycline-responsive disease or disorder, in a biological sample or in a subject. In certain embodiments, a pharmaceutical composition of this invention is formulated for administration to a subject in need of such pharmaceutical composition. The term "subject," as used herein, means an animal. In some embodiments, the animal is a mammal. In certain embodiments, the subject is a veterinary patient (i.e., a non-human mammal patient, such as a dog, a cat, a horse, a pig or a rodent, such as a mouse or rat). In some embodiments, the subject is a dog. In other embodiments, the subject is a human (e.g., a human patient).

The amount of the crystalline form of a compound represented by the bis HCl salt Structural Formula 1 that may be combined with the pharmaceutically acceptable carrier materials to produce a pharmaceutical composition in a single dosage form will vary depending upon the host treated and/or the particular mode of administration. In one embodiment, the pharmaceutical compositions should be formulated so that a dosage of between 0.01-100 mg/kg body weight/day of the compound of Structural Formula 1 can be administered to a patient receiving these compositions. In another embodiment, the dosage is from about 0.5 to about 100 mg/kg of body weight, or between 1 mg and 1000 mg/dose, every 4 to 120 hours, or according to the requirements of the particular drug. Typically, the pharmaceutical compositions of this invention will be administered from about 1 to about 6 times per day. Exemplary doses, include but are not limited to, 1.0 mg/kg twice a day for about 4-14 days and 1.5 mg/kg once a day for 5 to 10 days.

It should also be understood that a specific dosage and treatment regimen for any particular subject (e.g., patient) will depend upon a variety of factors, including the activity of the specific compound employed, the age, body weight, general health, sex, diet, time of administration, rate of excretion, drug combination, and the judgment of the treating physician and the severity of the particular disease being treated.

Upon improvement of a subject's condition, a maintenance dose of a pharmaceutical composition of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

Methods of Treatment and Uses for Pharmaceutical Compositions

Pharmaceutical compositions described herein are generally useful for treatment or prevention of a tetracycline-responsive disease or disorder. Thus, in certain embodiments, the invention provides a method for treating a tetracycline-responsive disease or disorder, comprising administering to a subject in need thereof a therapeutically effective amount of a crystalline form, such as a crystalline form, of the bis HCl salt of a compound of Structural Formula 1, or a pharmaceutical composition described herein. The compound of Structural Formula 1 or crystalline form thereof, pharmaceutical composition thereof or combination of the foregoing can also be administered to cells in culture, e.g., in vitro or ex vivo, or to a subject, e.g., in vivo, to treat, prevent, and/or diagnose a variety of disorders, including those described herein.

The term "treat" or "treating" means to alleviate symptoms, eliminate the causation of the symptoms, either on a temporary or permanent basis, or to slow the appearance of symptoms of the named disorder or condition.

The term "therapeutically effective amount" means an amount of the bis HCl salt of a compound of Structural Formula 1 or crystalline form thereof (typically, in a pharmaceutical composition described herein) which is effective in treating or lessening the severity of one or more symptoms of a disorder or condition.

"Tetracycline-responsive disease or disorder" refers to a disease or disorder that can be treated, prevented, or otherwise ameliorated by the administration of a tetracycline compound of the present invention. Tetracycline-responsive disease or disorder includes infections, cancer, inflammatory disorders, autoimmune disease, arteriosclerosis, corneal ulceration, emphysema, arthritis, osteoporosis, osteoarthritis, multiple sclerosis, osteosarcoma, osteomyelitis, bronchiectasis, chronic pulmonary obstructive disease, skin and eye diseases, periodontitis, osteoporosis, rheumatoid arthritis, ulcerative colitis, prostatitis, tumor growth and invasion, metastasis, diabetes, diabetic proteinuria, panbronchiolitis; aortic or vascular aneurysms, skin tissue wounds, dry eye, bone, cartilage degradation, malaria, senescence, diabetes, vascular stroke, neurodegenerative disorders, cardiac disease, juvenile diabetes, acute and chronic bronchitis, sinusitis, and respiratory infections, including the common cold; Wegener's granulomatosis; neutrophilic dermatoses and other inflammatory diseases such as dermatitis herpetiformis, leukocytoclastic vasculitis, bullous lupus erythematosus, pustular psoriasis, erythema elevatum diutinum; vitiligo; discoid lupus erythematosus; pyoderma gangrenosum; pustular psoriasis; blepharitis, or meibomianitis; Alzheimer's disease; degenerative maculopathy; acute and chronic gastroenteritis and colitis; acute and chronic cystitis and urethritis; acute and chronic dermatitis; acute and chronic conjunctivitis; acute and chronic serositis; uremic pericarditis; acute and chronic cholecystis; cystic fibrosis, acute and chronic vaginitis; acute and chronic uveitis; drug reactions; insect bites; burns and sunburn, bone mass disorder, acute lung injury, chronic lung disorders, ischemia, stroke or ischemic stroke, skin wound, aortic or vascular aneurysm, diabetic retinopathy, hemorrhagic stroke, angiogenesis, and other states for which tetracycline compounds have been found to be active (see, for example, U.S. Pat. Nos. 5,789,395; 5,834,450; 6,277,061 and 5,532,227, each of which is expressly incorporated herein by reference).

In addition, the invention relates to methods of treating any disease or disease state that could benefit from modulating the expression and/or function of nitric oxide, metalloproteases, proinflammatory mediators and cytokines, reactive oxygen species, components of the immune response, including chemotaxis, lymphocyte transformation, delayed hypersensitivity, antibody production, phagocytosis, and oxidative metabolism of phagocytes. A method to treat any disease or disease state that could benefit from modulating the expression and/or function of C-reactive protein, signaling pathways (e.g., FAK signaling pathway), and/or augment the expression of COX-2 and PGE2 production is covered. A method to treat any disease or disease state that could benefit from inhibition of neovascularization is covered.

In certain embodiments, compositions of the invention can be used to prevent or treat important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., Cancer Res., 48: 6686-6690 (1988)).

Infections that can be treated using compositions of the invention include, but are not limited to, skin infections, GI infections, urinary tract infections (e.g., complication UTI), complicated intra-abdominal infections, genito-urinary infections, respiratory tract infections, sinuses infections, middle ear infections, systemic infections, cholera, influenza, bronchitis, acne, malaria, sexually transmitted disease including syphilis and gonorrhea, Legionnaires' disease, Lyme disease, Rocky Mountain spotted fever, Q fever, typhus, bubonic plague, gas gangrene, hospital acquired infections, leptospirosis, whooping cough, anthrax and infections caused by the agents responsible for lymphogranuloma venereum, inclusion conjunctivitis, or psittacosis. Infections can be bacterial, fungal, parasitic and viral infections (including those which are resistant to other tetracycline compounds).

In one embodiment, the infection can be caused by bacteria. In another embodiment, the infection is caused by a Gram-positive bacteria. In a specific aspect of this embodiment, the infection is caused by a Gram-positive bacterium selected from *Staphylococcus* spp., *Streptococcus* spp., *Propionibacterium* spp., *Enterococcus* spp., *Bacillus* spp., *Corynebacterium* spp., *Nocardia* spp., *Clostridium* spp., *Actinobacteria* spp., and *Listeria* spp.

In another embodiment, the infection is caused by a Gram-negative bacterium. In one aspect of this embodiment, the infection is caused by a proteobacteria (e.g., Betaproteobacteria and Gammaproteobacteria), including *Escherichia coli*, *Salmonella*, *Shigella*, other Enterobacteriaceae, *Pseudomonas*, *Moraxella*, *Helicobacter*, *Stenotrophomonas*, *Bdellovibrio*, acetic acid bacteria, *Legionella* or alpha-proteobacteria such as *Wolbachia*. In another aspect, the infection is caused by a Gram-negative bacteria selected from cyanobacteria, spirochaetes, green sulfur or green non-sulfur bacteria. In a specific aspect of this embodiment, the infection is caused by a Gram-negative bacteria selected from Enterobactericeae (e.g., *E. coli*, *Klebsiella pneumonia* including those containing extended-spectrum .beta.-lactamases and/or carbapenemases), Bacteroidaceae (e.g., *Bacteroides fragilis*), Vibrionaceae (*Vibrio cholerae*), Pasteurellae (e.g., *Haemophilus influenza*), Pseudomonadaceae (e.g., *Pseudomonas aeruginosa*), Neisseriaceae (e.g. *Neisseria meningitidis*), Rickettsiae, Moraxellaceae (e.g., *Moraxella catarrhalis*), any species of Proteeae, *Acinetobacter* spp., *Helicobacter* spp., and *Campylobacter* spp.

In a particular embodiment, the infection is caused by Gram-negative bacterium selected from the group consisting of Enterobactericeae (e.g., *E. coli*, *Klebsiella pneumoniae*), *Pseudomonas*, and *Acinetobacter* spp.

In another embodiment, the infection is caused by an organism selected from the group consisting of *K. pneumoniae*, *Salmonella*, *E. hirae*, *A. baumanii*, *M. catarrhalis*, *H. influenzae*, *P. aeruginosa*, *E. faecium*, *E. coli*, *S. aureus*, and *E. faecalis*.

In another embodiment, the infection is caused by an organism selected from the group consisting of rickettsiae, chlamydiae, *Legionella* spp. and *Mycoplasma* spp.

In another embodiment, the infection is caused by an organism resistant to tetracycline or any member of first and second generation of tetracycline antibiotics (e.g., doxycycline or minocycline).

In another embodiment, the infection is caused by an organism resistant to methicillin.

In another embodiment, the infection is caused by an organism resistant to vancomycin.

In another embodiment, the infection is caused by an organism resistant to a quinolone or fluoroquinolone.

In another embodiment, the infection is caused by an organism resistant to tigecycline.

In another embodiment, the infection is caused by a multidrug-resistant pathogen (having intermediate or full resistance to any two or more antibiotics). In another embodiment the infection is a *Bacillus anthracis* infection. "*Bacillus anthracis* infection" includes any state, diseases, or disorders caused or which result from exposure or alleged exposure to *Bacillus anthracis* or another member of the *Bacillus cereus* group of bacteria. In another embodiment, the infection is caused by *Bacillus anthracis* (anthrax), *Yersinia pestis* (plague), or *Francisella tularensis* (tularemia).

In yet another embodiment, the infection can be caused by more than one organism described above. Examples of such infections include, but are not limited to, intra-abdominal infections (often a mixture of a gram-negative species like *E. coli* and an anaerobe like *B. fragilis*), diabetic foot (various combinations of *Streptococcus*, *Serratia*, *Staphylococcus* and *Enterococcus* spp., anaerobes (S. E. Dowd, et al., PloS one 2008; 3:e3326) and respiratory disease (especially in patients that have chronic infections like cystic fibrosis— e.g., *S. aureus* plus *P. aeruginosa* or H *influenza*, atypical pathogens), wounds and abscesses (various gram-negative and gram-positive bacteria, notably MSSA/MRSA, coagulase-negative staphylococci, enterococci, *Acinetobacter*, *P. aeruginosa*, *E. coli*, *B. fragilis*), and bloodstream infections (13% were polymicrobial (H. Wisplinghoff, et al., Clin. Infect. Dis. 2004; 39:311-317)).

In a further embodiment, the tetracycline responsive disease or disorder is not a bacterial infection. In another embodiment, the compositions of the invention are essentially non-antibacterial. For example, non-antibacterial compositions may have MIC values greater than about 4 µg/mL. In another embodiment, the compositions of the invention have both antibacterial and non-antibacterial effects.

Tetracycline responsive disease or disorder also includes diseases or disorders associated with inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, microorganisms, tissue necrosis, cancer or other agents. Acute inflammation is short-lasting, lasting only a few days. If it is longer lasting however, then it may be referred to as chronic inflammation.

IPASs include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders can be treated using the compounds of the invention or a pharmaceutically acceptable salt thereof include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; inflammatory bowel disorder; acute and chronic cystitis and urethritis; vasculitis; sepsis; nephritis; pancreatitis; hepatitis; lupus; inflammatory skin disorders including, for example, eczema, dermatitis, psoriasis, pyoderma gangrenosum, acne rosacea, and acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

IPASs also include matrix metalloproteinase associated states (MMPAS). MMPAS include states characterized by aberrant amounts of MMPs or MMP activity.

Examples of matrix metalloproteinase associated states ("MMPASs") can be treated using compositions of the invention include, but are not limited to, arteriosclerosis, corneal ulceration, emphysema, osteoarthritis, multiple sclerosis (Liedtke et al., Ann. Neurol. 1998, 44: 35-46; Chandler et al., J. Neuroimmunol. 1997, 72: 155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., Annu. Rev. Cell Biol. 1993, 9: 541-73; Tryggvason et al., Biochim. Biophys. Acta 1987, 907: 191-217; Li et al., Mol. Carcillog. 1998, 22: 84-89)), metastasis, acute lung injury, stroke, ischemia, diabetes, aortic or vascular aneurysms, skin tissue wounds, dry eye, bone and cartilage degradation (Greenwald et al., Bone 1998,22: 33-38; Ryan et al., Curr. Op. Rheumatol. 1996, 8: 238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In a further embodiment, the IPAS includes disorders described in U.S. Pat. Nos. 5,929,055; and 5,532,227, incorporated herein by reference in their entirety.

Tetracycline responsive disease or disorder also includes diseases or disorders associated with NO associated states. The term "NO associated states" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789,395 are also included as NO associated states. The entire contents of each of these patents are hereby incorporated herein by reference.

Examples of diseases or disorders associated with NO associated states can be treated using the compositions of the invention include, but are not limited to, malaria, senescence, diabetes, vascular stroke, neurodegenerative disorders (Alzheimer's disease and Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

In another embodiment, the tetracycline responsive disease or disorder is cancer. Examples of cancers that can be treated using the compounds of the invention or a pharmaceutically acceptable salt thereof include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostate carcinoma, lung cancer, and a variety of other cancers as well. The methods of the invention also cause the inhibition of cancer growth in adenocarcinomas, such as, for example, those of the prostate, breast, kidney, ovary, testes, and colon. In one embodiment, the cancers treated by methods of the invention include those described in U.S. Pat. Nos. 6,100,248; 5,843,925; 5,837,696; or 5,668,122, incorporated herein by reference in their entirety.

Alternatively, the compositions may be useful for preventing or reducing the likelihood of cancer recurrence, for example, to treat residual cancer following surgical resection or radiation therapy. The compositions useful according to the invention are especially advantageous as they are substantially non-toxic compared to other cancer treatments.

In a further embodiment, the compositions of the invention are administered in combination with standard cancer therapy, such as, but not limited to, chemotherapy.

Examples of tetracycline responsive states can be treated using the compositions of the invention or a pharmaceutically acceptable salt thereof also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amyotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoffs psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity.

Further neurological disorders include, for example, those listed in the American Psychiatric Association's Diagnostic and Statistical manual of Mental Disorders (DSM), the most current version of which is incorporated herein by reference in its entirety.

In another embodiment, the tetracycline responsive disease or disorder is diabetes. Diabetes that can be treated using the compositions of the invention include, but are not limited to, juvenile diabetes, diabetes mellitus, diabetes type I, or diabetes type II. In a further embodiment, protein glycosylation is not affected by the administration of the compositions of the invention. In another embodiment, the composition of the invention is administered in combination with standard diabetic therapies, such as, but not limited to insulin therapy.

In another embodiment, the tetracycline responsive disease or disorder is a bone mass disorder. Bone mass disorders that can be treated using the compounds of the invention or a pharmaceutically acceptable salt thereof include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the compositions of the invention. In a further embodiment, the bone mass disorders include those described in U.S. Pat. Nos. 5,459,135; 5,231,017; 5,998,390; 5,770,588; RE 34,656; 5,308,839; 4,925,833; 3,304,227; and 4,666,897, each of which is hereby incorporated herein by reference in its entirety.

In another embodiment, the tetracycline responsive disease or disorder is acute lung injury. Acute lung injuries that can be treated using the compounds of the invention or a pharmaceutically acceptable salt thereof include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The tetracycline responsive disease or disorders of the invention also include chronic lung disorders. Examples of chronic lung disorders that can be treated using the compounds of the invention or a pharmaceutically acceptable salt thereof include, but are not limited, to asthma, cystic fibrosis, chronic obstructive pulmonary disease (COPD), and emphysema. In a further embodiment, the acute and/or chronic lung disorders that can be treated using the compositions of the invention include those described in U.S. Pat. Nos. 5,977,091; 6,043,231; 5,523,297; and 5,773,430, each of which is hereby incorporated herein by reference in its entirety.

In yet another embodiment, the tetracycline responsive disease or disorder is ischemia, stroke, or ischemic stroke.

In a further embodiment, the compositions of the invention can be used to treat such disorders as described above and in U.S. Pat. Nos. 6,231,894; 5,773,430; 5,919,775 and 5,789,395, incorporated herein by reference.

In another embodiment, the tetracycline responsive disease or disorder is a skin wound. The invention also provides a method for improving the healing response of the epithelialized tissue (e.g., skin, mucosae) to acute traumatic injury (e.g., cut, burn, scrape, etc.). The method includes using a composition of the invention to improve the capacity of the epithelialized tissue to heal acute wounds. The method may increase the rate of collagen accumulation of the healing tissue. The method may also decrease the proteolytic activity in the epithelialized tissue by decreasing the collagenolytic and/or gellatinolytic activity of MMPs. In a further embodiment, the tetracycline compound of the invention or a pharmaceutically acceptable salt thereof is administered to the surface of the skin (e.g., topically). In a further embodiment, the compositions of the invention are used to treat a skin wound, and other such disorders as described in, for example, U.S. Pat. Nos. 5,827,840; 4,704,383; 4,935,412; 5,258,371; 5,308,839, 5,459,135; 5,532,227; and 6,015,804; each of which is incorporated herein by reference in its entirety.

In yet another embodiment, the tetracycline responsive disease or disorder is an aortic or vascular aneurysm in vascular tissue of a subject (e.g., a subject having or at risk of having an aortic or vascular aneurysm, etc.). The compositions may be effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the compositions of the invention are used to treat disorders described in U.S. Pat. Nos. 6,043,225 and 5,834,449, incorporated herein by reference in their entirety.

In still another embodiment, the compounds, compositons and pharmaceutical compositins of the invention can be used to treat oral mucositis. In a particular aspect, the oral mucositis is a result of chemotherapy, radiation or both. In another particular aspect, the subject having oral mucositis is undergoing chemotherapy and/or radiation therapy for head and neck cancer. In a specific aspect, the head and neck cancer is selected from: laryngeal; hypopharyngeal; nasal cavity; paranasal sinus; nasopharyngeal; oral; oropharyngeal; and salivary gland.

Combination Therapies

In some embodiments, a crystalline form of a compound represented by the bis HCl salt Structural Formula 1 (e.g., Form A, B, I or J) is administered together with an additional "second" therapeutic agent or treatment. The choice of second therapeutic agent may be made from any agent that is typically used in a monotherapy to treat the indicated disease or condition. As used herein, the term "administered together" and related terms refers to the simultaneous or sequential administration of therapeutic agents in accordance with this invention. For example, the compound of Structural Formula 1 may be administered with another therapeutic agent simultaneously or sequentially in separate unit dosage forms or together in a unit dosage form. Accordingly, the invention provides a unit dosage form comprising a crystalline form of a compound represented by the bis HCl salt of Structural Formula 1 (e.g., Form A, B, I or J), an additional therapeutic agent, and a pharmaceutically acceptable carrier.

In one embodiment, where a second therapeutic agent is administered to a subject, the effective amount of the crystalline form of a compound represented by the bis HCl salt of Structural Formula 1 is less than its effective amount would be where the second therapeutic agent is not administered. In another embodiment, the effective amount of the second therapeutic agent is less than its effective amount would be were the crystalline form of a compound represented by the bis HCl salt of Structural Formula 1 not administered. In this way, undesired side effects associated with high doses of either agent may be minimized. Other potential advantages (including without limitation improved dosing regimens and/or reduced drug cost) will be apparent to those of skill in the art.

Synthetic Methods

Also provided herein are synthetic methods for preparing crystalline forms of a compound represented by the bis HCl salt of Structural Formula 1. In some aspects, a mixture of crystalline forms is produced. For example, the mixture may comprise two or more crystalline forms selected from Form A, Form B, Form I, or Form J, more specifically, two or more crystalline forms selected from Form B, Form I, or Form J. In some aspects, the mixture does not comprise Form A.

FORM B:

In one embodiment, the invention relates to a method of preparing a crystalline form of the bis-HCl salt of a compound represented by Structural Formula 1:

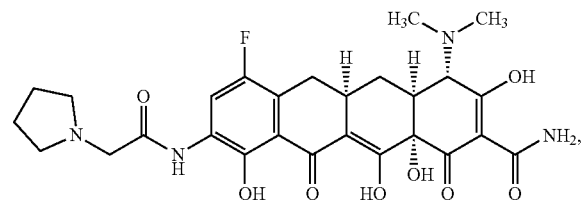

(1)

wherein the crystalline form is Form B and is characterized by at least three x-ray powder diffraction peaks at 2θ angles selected from 9.19°, 9.66°, 23.32°, and 24.35°, the method comprising:
(a) adding together the free base, amorphous form of a compound of Structural Formula 1 and a solvent mixture comprising methanol, a first portion of ethanol, water and concentrated HCl, thereby forming a recrystallization mixture of amorphous compound;
(b) adding a second portion of ethanol to the recrystallization mixture with stirring at a sufficient amount, for a sufficient time and at a sufficient temperature to form particles of crystalline Form B; and
(c) isolating the particles of crystalline Form B, thereby preparing a composition comprising particles of crystalline Form B of the bis HCl salt of the compound of Structural Formula 1.

In certain aspects of the method of preparing Form B, the ratio by volume of methanol, first portion of ethanol, water and concentrated HCl in the recrystallization mixture is from about 1 to about 8 (methanol), from about 1 to about 3 (ethanol), from about 0.1 to about 1.0 (water) and from about 0.1 to about 2 (concentrated HCl) by volume. In a specific aspect, the volume of the second portion of ethanol is about from about 4 to about 6 times the volume of the first portion of ethanol.

In another aspect of the method of preparing Form B, stirring of the recrystallization mixture (both with and without the addition of the second portion of ethanol) is conducted at a temperature from about 15° C. to about 25° C.

In another aspect of the method of preparing Form B, the particles are isolated by filtration.

In yet another aspect, the method of preparing Form B further comprises step washing the particles of crystalline Form B, for example, with ethanol or the mixture of methanol, water, and concentrated HCl.

Form I:

In certain embodiments, the invention relates to a method of preparing a crystalline form of the bis-HCl salt of a compound represented by Structural Formula 1:

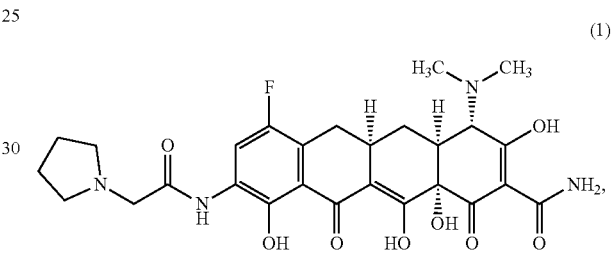

(1)

wherein the crystalline form is Form I and is characterized by at least three x-ray powder diffraction peaks at 2θ angles selected from 7.22°, 7.80°, 10.41°, and 11.11°, the method comprising:
(a) suspending crystalline Form B of the compound of Structural Formula 1 in a mixture of ethanol, water, and concentrated HCl, thereby forming a slurry of Form B;
(b) stirring the slurry of Form B for a sufficient time and at a sufficient temperature to form a slurry of crystalline Form I particles; and
(c) isolating the particles of crystalline Form I.

In certain aspects of the method of preparing Form I, the ratio of ethanol to water to concentrated HCl by volume in the mixture of ethanol, water, and concentrated HCl is about 4.0-6.0 to about 0.3-0.5 to about 0.3-0.5, for example, about 5.0 to about 0.4 to about 0.4, or about 5.0 to about 0.4 to about 0.35.

In other aspects, the method of preparing Form I further comprises step (b') adding to the slurry of Form B an amount of the crystalline Form I, thereby forming a seeded mixture.

In another aspect of the method of preparing Form I, stirring the slurry of Form B or the seeded mixture is conducted at a temperature from about 18° C. to about 25° C. for about 12 h to about 40 h.

In certain aspects, the method of preparing Form I further comprises step (b″) adding to the slurry of Form I an anti-solvent, thereby forming an anti-solvent slurry. For example, the anti-solvent can be ethanol. In a particular aspect, the anti-solvent is ethanol, and is added over about 1 hour to about 15 hours (such as about 1 hour to about 5 hours), for example, over about 1 hour, 3 hours or 10 hours.

In another aspect of the method of preparing Form I, the particles are isolated by filtration.

In certain aspects, the method of preparing Form I further comprises step (c') washing the solid particles, for example, with ethanol, or the mixture of ethanol, water, and concentrated HCl.

In certain embodiments, the invention relates to a method of preparing a crystalline form of the bis-HCl salt of a compound represented by Structural Formula 1:

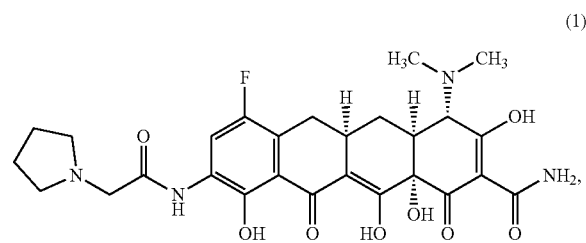 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]

(1)

wherein the crystalline form is Form J and is characterized by at least three x-ray powder diffraction peaks at 2θ angles selected from 7.02°, 7.80°, 22.13°, and 23.22°, the method comprising:
(a) exposing crystalline Form I to a temperature from about 20° C. to about 45° C. at a relative humidity of about 70% to about 90%; and
(b) isolating particles of crystalline Form J.

In certain aspects of the method of preparing Form J, crystalline Form I is exposed to a temperature of about 40° C. and a relative humidity of about 75%.

In other aspects of the method of preparing Form J, crystalline Form I is exposed to a temperature of about 25° C. and a relative humidity from about 75% to about 85%.

In certain embodiments, the invention relates to a method of preparing a crystalline form of the bis-HCl salt of a compound represented by Structural Formula 1:

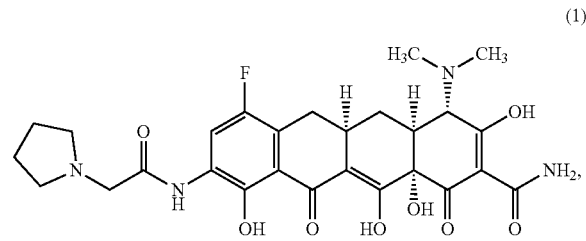 [SMILES: CN(C)[C@@H]1C(O)=C(C(N)=O)C(=O)[C@@]2(O)C(O)=C3C(=O)c4c(O)c(NC(=O)CN5CCCC5)cc(F)c4C[C@H]3C[C@@H]12]

(1)

wherein the crystalline form is Form A and is characterized by at least three x-ray powder diffraction peaks at 2θ angles selected from 3.31°, 6.01°, 6.33°, and 8.73°, the method comprising:
(a) combining together with stirring the bis-HCl salt of a compound of Structural Formula 1 in amorphous form and a solvent mixture of ethanol and water, thereby forming a solution of amorphous compound;
(b) adding to the solution of amorphous compound concentrated HCl and methanol and stirring, thereby forming a slurry;
(c) adding to the slurry an anti-solvent, thereby forming a slurry of crystalline Form A; and
(d) isolating the solid particles of crystalline Form A, thereby preparing a composition comprising particles of crystalline Form A of the compound of Structural Formula 1.

In certain aspects of the method of preparing Form A, the ratio of ethanol to water by volume in the mixture of ethanol and water is about 3.0-5.0 to about 0.3-0.5, for example, about 4.0 to about 0.4.

In certain aspects of the method of preparing Form A, the ratio of concentrated HCl to methanol by volume is about 0.2-0.4 to about 0.1-0.4, for example, about 0.3 to about 0.2.

In other aspects, the method of preparing Form A further comprises steps (b') adding to the slurry of amorphous compound an amount of the crystalline Form A, thereby forming a seeded mixture; and (b") stirring the seeded mixture at a temperature from about 20° C. to about 25° C. for about 1 h to about 24 h.

In certain aspects of the method of preparing Form A, the anti-solvent is ethanol. In a more particular aspect, the anti-solvent is added over from about 2 h to about 6 h, for example, over about 4 h.

In another aspect, the method of preparing Form A further comprising step (c') cooling the slurry of Form A to about 0° C.

In certain embodiments, the invention relates to any of the methods described herein (methods to produce crystalline Forms I, B, J or A), further comprising step drying the isolated particles, for example at about 22° C. to about 30° C. for about 12 h to about 5 days (e.g., from about 12 h to about 24 h) at about 26° C. for about 18 h, or under nitrogen gas for about 1 h to about 20 h, then under vacuum conditions for about 15 h to about 25 h, or under nitrogen gas for about 1 h, then under vacuum conditions for about 20 h, or under nitrogen gas for about 10 h, then under vacuum conditions at about 25° C.

"Solvent system," as used herein, refers to a single solvent or a mixture of two or more (typically, two) different solvents. Exemplary solvents for a solvent system include water and organic solvents such as, but not limited to, methanol, ethanol, diisopropyl ether, 2-propanol, ethyl acetate, and isopropyl acetate.

"Inducing formation," used herein, includes any conditions that induce the compound of Structural Formula 1 to crystallize as the specified crystalline form, for example, crystalline Form B or crystalline Form I. Inducing formation includes merely allowing solid particles of the specified crystalline form to precipitate from a solution or slurry, for example, without actively performing any step. Inducing formation also includes maturing (e.g., aging, with or without cooling, and/or cycling) a solution comprising a compound of Structural Formula 1 in an appropriate solvent system and/or allowing a solution comprising a compound of Structural Formula 1 in an appropriate solvent system to slowly evaporate, with or without cooling. Inducing formation also includes cooling the compound of Structural Formula 1 or a solution including the compound of Structural Formula 1. Other methods of inducing formation of a crystalline solid are known in the art and include, for example, the use of anti-solvents and vapor diffusion. In preferred embodiments, inducing formation comprises cooling the compound of Structural Formula 1 or a solution or slurry including the compound of Structural Formula 1 in an appropriate solvent system.

Isolating the solid particles of crystalline Form B, Form I, Form J, or Form A is typically effected by filtration and, optionally, rinsing of the filtered solids with a solvent (e.g., a chilled solvent), although other means of isolating the solid particles are known in the art. Other means of isolating the solid particles of crystalline Form B, Form I, Form J, or Form A include, but are not limited to, distilling liquid away from the solid particles or otherwise drying the solid particles, for example, by heating, by subjecting to reduced pressure (e.g., in vacuo) or any combination of the foregoing.

"Room temperature" and "ambient temperature," as used herein, means a temperature of from about 16° C. to about 25° C.

"Ambient conditions," as used herein, refers to room temperature and atmospheric pressure conditions.

Drying crystalline Form B, Form I, Form J, or Form A of the compound of Structural Formula 1 or a mixture comprising two or more crystalline forms of the compound of Structural Formula 1 can be accomplished, for example, by distilling any liquid present away from the solid crystalline form(s), by exposing the solid crystalline form(s) to ambient conditions or passing a stream of gas, such as nitrogen gas, over the solid crystalline form(s) (and thereby inducing the evaporation or desolvation of any liquid or entrapped volatile substance), by subjecting the solid crystalline form(s) to reduced pressure (e.g., in vacuo) or any combination of the foregoing. Crystalline Form I, in particular, can be converted to crystalline Form J by drying under conditions in which ethanol can desolvate from crystalline Form I, for example, by subjecting crystalline Form I to reduced pressure (e.g., in vacuo) or by exposing crystalline Form I to ambient conditions or passing a stream of gas over crystalline Form I.

It is understood that, quite often, in practice, the steps for preparing crystalline Form B, Form I, Form J, or Form A according to the methods described herein entail a combination of heating, maturing and/or drying.

EXEMPLIFICATION

General Materials and Methods

As used herein, TP-434-046 is the bis-HCl salt of the compound represented by structural Formula 1.

XRPD

The data presented in this application contain x-ray diffraction patterns with labeled peaks and tables with peak lists. The range of data collected is instrument dependent. Under most circumstances, peaks within the range of up to about 30° 2θ were selected. Rounding algorithms were used to round each peak to the nearest 0.1° or 0.01° 2θ, depending upon the instrument used to collect the data and/or the inherent peak resolution. The location of the peaks along the x-axis (° 2θ) in both the figures and the tables were determined using proprietary software (TRIADS™ v2.0) and rounded to one or two significant figures after the decimal point based upon the above criteria. Peak position variabilities are given to within ±0.2° 2Θ based upon recommendations outlined in the USP discussion of variability in x-ray powder diffraction (United States Pharmacopeia, USP 38-NF 33 through S1, <941> Aug. 1, 2015). For d-space listings, the wavelength used to calculate d-spacings was 1.5405929 Å, the Cu—$K_{α1}$ wavelength (*Phys. Rev.* A56(6) 4554-4568 (1997)). Variability associated with d-spacing estimates was calculated from the USP recommendation, at each d-spacing, and provided in the respective tables.

Per USP guidelines, variable hydrates and solvates may display peak variances greater than 0.2° 2θ and therefore peak variances of 0.2° 2θ are not applicable to these materials.

"Prominent Peaks" are a subset of the entire observed peak list. Prominent peaks are selected from observed peaks by identifying preferably non-overlapping, low-angle peaks, with strong intensity.

If multiple diffraction patterns are available, then assessments of particle statistics (PS) and/or preferred orientation (PO) are possible. Reproducibility among XRPD patterns from multiple samples analyzed on a single diffractometer indicates that the particle statistics are adequate. Consistency of relative intensity among XRPD patterns from multiple diffractometers indicates good orientation statistics. Alternatively, the observed XRPD pattern may be compared with a calculated XRPD pattern based upon a crystal structure, if available. Two-dimensional scattering patterns using area detectors can also be used to evaluate PS/PO. If the effects of both PS and PO are determined to be negligible, then the XRPD pattern is representative of the powder average intensity for the sample and prominent peaks may be identified as "Representative Peaks." In general, the more data collected to determine Representative Peaks, the more confident one can be of the classification of those peaks.

"Characteristic peaks," to the extent they exist, are a subset of Representative Peaks and are used to differentiate one crystalline polymorph from another crystalline polymorph (polymorphs being crystalline forms having the same chemical composition). Characteristic peaks are determined by evaluating which representative peaks, if any, are present in one crystalline polymorph of a compound against all other known crystalline polymorphs of that compound to within ±0.2° 2θ. Not all crystalline polymorphs of a compound necessarily have at least one characteristic peak.

TG

TG analyses for the crystalline Forms A, I and J described herein were performed using a TA Instruments 2050 thermogravimetric analyzer. Temperature calibration was performed using nickel and Alumel™. Each sample was placed in a platinum pan and inserted into the TG furnace. The furnace was heated under a nitrogen purge. The data acquisition parameters are displayed above each thermogram in the figures. The method code on the thermogram is an abbreviation for the start and end temperature as well as the heating rate; e.g., 00-350-10 means "ambient to 350° C., at 10° C./min."

TG analyses for crystalline Form B was conducted as a TG-FTIR using Netzsch Thermo-Microbalance TG 209 with Bruker FT-IR Spectrometer Vector 22. Al-crucible (open or with micro hole), $N_2$ atmosphere, heating rate 10° C. $min^{-1}$

DSC

DSC for the crystalline Forms A, I and J described herein was performed using a TA Instruments Q2000 differential scanning calorimeter. Temperature calibration was performed using NIST-traceable indium metal. Each sample was placed into an aluminum Tzero crimped (T0C) DSC pan, covered with a lid, and the weight was accurately recorded. A weighed aluminum pan configured as the sample pan was placed on the reference side of the cell. The data acquisition parameters and pan configuration for each thermogram are displayed in the Figures. The method code on the thermogram is an abbreviation for the start and end temperature as well as the heating rate, e.g., 30-250-10 means "from −30° C. to 250° C., at 10° C./min." Other abbreviations: T0C=Tzero crimped pan; HS=lid hermetically sealed; HSLP=lid hermetically sealed and perforated with a laser pinhole; C=lid crimped; NC=lid not crimped.

DSC for crystalline Form B described herein was performed using Perkin Elmer DSC 7 with closed Au crucibles, heating rate: 10 or 20° C. $min^{-1}$, range: −50° C. to 250° C.

Example 1—Form A

Preparation of Form a without Seeding

Amorphous TP-434-046 (bis HCl salt) was obtained according to the procedures detailed in U.S. Pat. No. 8,906,887, the entire content of which is hereby incorporated by reference. Amorphous TP-434-046 was stirred in a mixture of HCl in methanol (1.25 M, 1V) and HCl in EtOH (1.25 M, 2V) for about 10 minutes, followed by the addition of ethanol (4V). The suspension was stirred at ambient temperature overnight, and then cooled to 0° C. Form A was then isolated.

Preparation of Form a with Seeding

Second Generation Process—Form A

The crystallization process was started by dissolving TP-434-046 (the bis HCl salt) in a mixture of methanol/ethanol/water/conc. HCl (1.91V/0.84V/0.19V/0.47V) between 0° to 22° C., followed by polish filtration and rinsing with ethanol (1.75V). The solution was then seeded with Form A and stirred at ambient temperature for 2 hours to give a suspension. Additional ethanol (5.4V to 1 part of TP-434-046) was then added over a period of 1 hour and the mixture was continuously stirred for 3 hours. After cooling to 0° C. and stirring at 0° C. for 3 hours, the solid was isolated by filtration.

Third Generation Process—Form A

In 3rd generation Form A crystallization process amorphous TP-434-046 (bis HCl Salt) was dissolved in a mixture of EtOH/water (3.5V/0.4V), followed by polish filtration and rinsing with a solution of EtOH/Conc.HCl/MeOH (1.5V/0.3V/0.1V). The solution was then seeded with Form A and stirred overnight. Additional ethanol (4V) was added over a period of 4 hours. After stirring at ambient temperature for 1 more hour, the suspension was cooled to 0° C. and stirred at 0° C. for 2 hours and then isolated.

Form A is a co-solvate with EtOH and water

The XRPD patterns of Form A is depicted in FIG. 1, and the peaks are tabulated in Table 1.

TABLE 1

| °2θ | d space (Å) | Intensity (%) |
| --- | --- | --- |
| 3.31 ± 0.20 | 26.651 ± 1.609 | 17 |
| 5.28 ± 0.20 | 16.739 ± 0.634 | 9 |
| 6.01 ± 0.20 | 14.705 ± 0.489 | 100 |
| 6.33 ± 0.20 | 13.954 ± 0.441 | 45 |
| 8.28 ± 0.20 | 10.669 ± 0.257 | 5 |
| 8.73 ± 0.20 | 10.121 ± 0.231 | 23 |
| 9.19 ± 0.20 | 9.615 ± 0.209 | 5 |
| 9.50 ± 0.20 | 9.307 ± 0.196 | 6 |
| 10.01 ± 0.20 | 8.830 ± 0.176 | 6 |
| 10.49 ± 0.20 | 8.425 ± 0.160 | 19 |
| 11.62 ± 0.20 | 7.608 ± 0.130 | 6 |
| 11.88 ± 0.20 | 7.445 ± 0.125 | 14 |
| 12.32 ± 0.20 | 7.177 ± 0.116 | 4 |
| 12.89 ± 0.20 | 6.863 ± 0.106 | 8 |
| 13.36 ± 0.20 | 6.624 ± 0.099 | 5 |
| 13.65 ± 0.20 | 6.484 ± 0.095 | 15 |
| 14.06 ± 0.20 | 6.293 ± 0.089 | 19 |
| 14.23 ± 0.20 | 6.219 ± 0.087 | 11 |
| 14.79 ± 0.20 | 5.983 ± 0.080 | 5 |
| 15.22 ± 0.20 | 5.818 ± 0.076 | 15 |
| 15.46 ± 0.20 | 5.726 ± 0.074 | 14 |
| 16.21 ± 0.20 | 5.464 ± 0.067 | 14 |
| 16.55 ± 0.20 | 5.353 ± 0.064 | 18 |

Figure 2A:
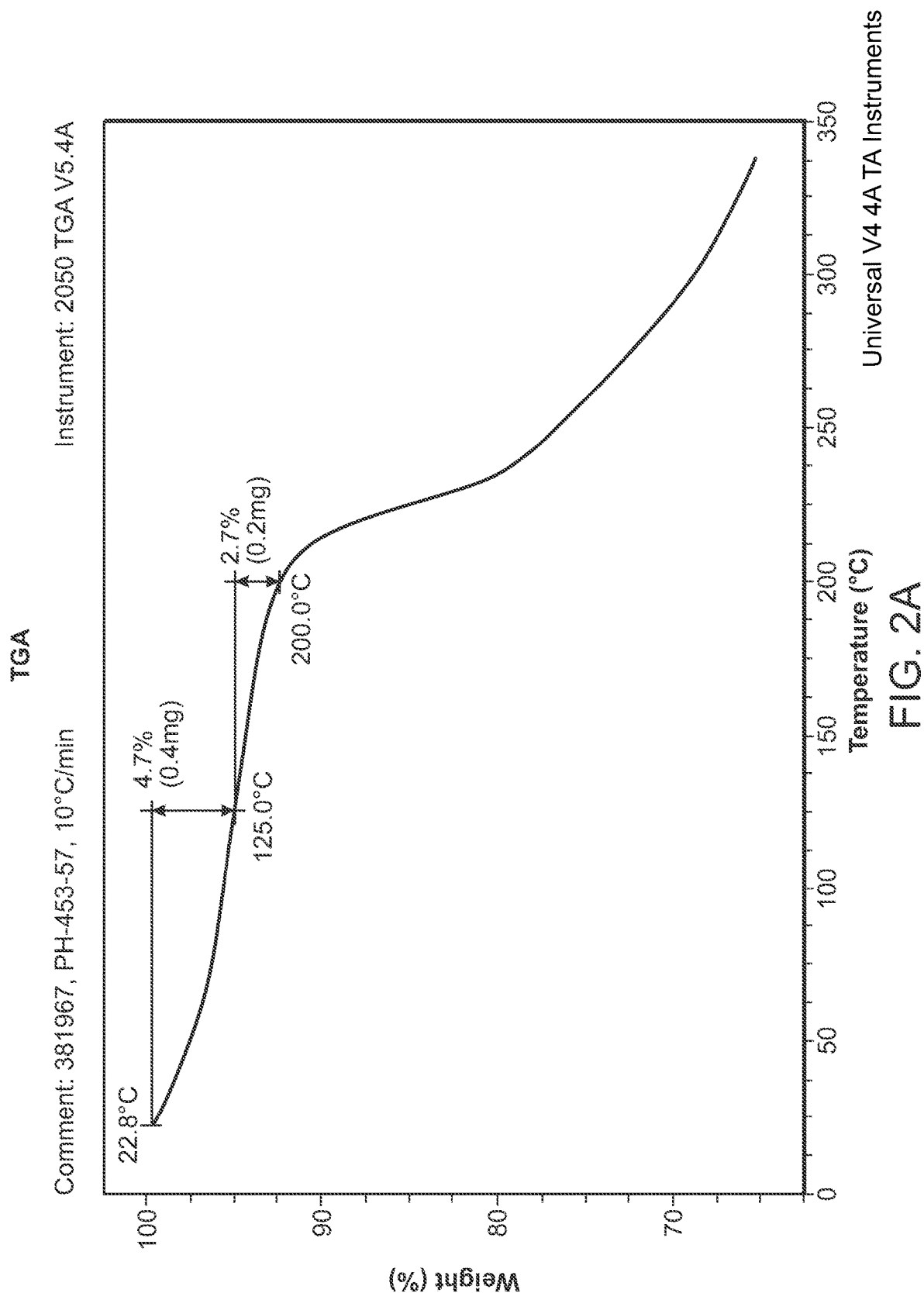
FIG. 2A is a thermogravimetric analysis (TGA) thermogram of Structural Formula 1—Form A.

The TGA trace of one of the batches of Form A is depicted in FIG. 2A. Weight losses of approximately 4.7% from ambient to 125° C. and 2.7% from 125 to 200° C. were observed in the TG thermogram. Weight loss occurring above 200° C. is likely due to decomposition.

Figure 2B:
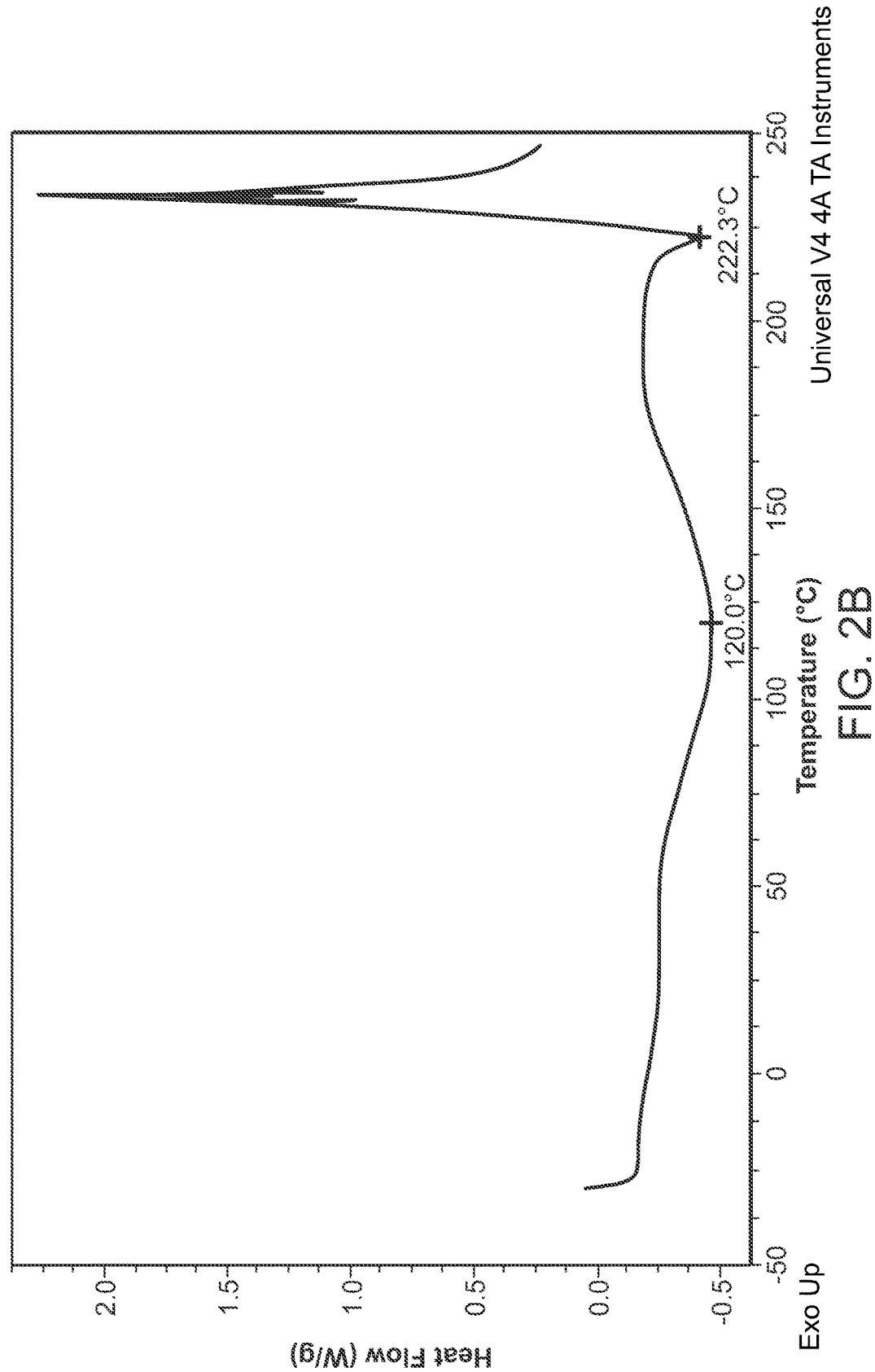
FIG. 2B is a differential scanning calorimetry (DSC) thermogram of Structural Formula 1—Form A.

The DSC trace of Form A is depicted in FIG. 2B. The DSC thermogram displays a broad endotherm at approximately 120° C. that correlates to the TG data. There is also an endotherm displayed at approximately 222° C. that may be due to a melt/decomposition.

Example 2—Form B

Preparation of Form B without Seeding
Conversion of TP-434-Freebase to TP-434-046 Form B

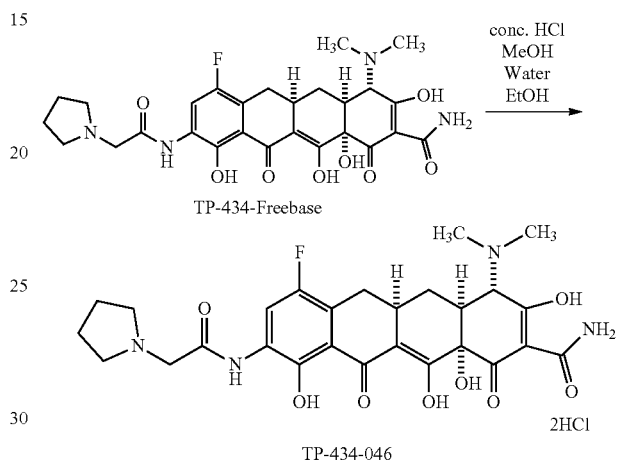

Procedure:

To a 5 L dried flask was charged 814 ml anhydrous methanol, followed by 358 mL 200 proof anhydrous ethanol. The mixture was cooled to 0 to 2° C. Water (81 mL) was charged followed by 199.7 ml 37% concentrated HCl. Temperature rose from 1.8° C. to 19.0° C. After temperature of the reaction mixture returned to 0° C., TP-434 freebase (426 g, about 0.763 moles,) was charged as a solid slowly over 30 minutes with temperature maintained below 20° C.

Solid suspension appears after only 4 minutes and microscope shows plate like crystal (Form B) formed. The yellow suspension was stirred for 2 hours at 20 to 23° C.

Anhydrous 200 proof ethanol (1.91 L) was added over 3 hours into the mixture. The resulted yellow suspension was cooled to 0 to 1° C. over 1 hour and the suspension was continuously stirred at 0 to 2° C. for 30 minutes.

The solid was collected by filtration through "M" fritted filter funnel. The solid cake was washed with 250 ml anhydrous 200 proof ethanol. After the wash, the cake was continuously dried in the filter funnel by pulling vacuum with nitrogen blanket for 14 hours.

The solid (610 g) was transferred into two trays and dry in high vacuum oven at room temperature (25±5° C.) until achieving constant weight (took about 24 hours) to give a yellow solid (466 g). KF is 6.2%. $^1$H-NMR showed the molar ratio of TP-434-046/MeOH/EtOH was 1/0.97/0.16.

The solid (459 g) was further dried under vacuum with humidity (with a beaker of water in the drying oven, 60-80% humidity, vacuum 0.043 mpa) for one day and then dried under vacuum by oil pump for two days to afford TP-434-046 as light yellow solid (458 g).

HPLC of product showed 98.88% TP-434. Assay of w/w showed the product contained 75.3% TP-434 Freebase. (Based on the w/w assay of the product, the yield of the crystallization is as least 81% without w/w assay correction of the starting material.) The residual methanol was 1.3 wt % and ethanol was not detected by $^1$H-NMR. The residue water by KF was 11.18%. CHN and chloride analysis showed C, 45.07%; H, 5.80%; N, 7.88%; Cl−, 9.88%. Calc. for $C_{27}H_{33}C_{12}F_1N_4O_8+5H_2O$: C, 44.94%; H, 6.01%; N, 7.76%; Cl−, 9.83; water, 12.5%. The XRPD of product was consistent with Form B.

Preparation of Form B with Seeding

Crude TP-434-046 was dissolved in methanol (6V). The solution was polish filtered through a 0.45 μm inline filter and rinsed with a solution of methanol (1V), water (0.56V) and concentrated HCl (0.16V). The solution was seeded with Form B seeds (0.5 wt %) prepared as described above and stirred at 21±2° C. for approximately 4 hours. Polished filtered concentrated HCl (0.28V) was added slowly with temperature controlled at 21±2° C. The mixture was stirred at 21±2° C. for about 16 hours, cooled to 0° C. in about 30 minutes and held at 0° C. for 3 hours. The solid was collected by filtration, washed with a solution of MeOH/ water/concentrated HCl (2×1V, 0.87/0.07/0.06). The solid (Form B) was dried under both vacuum and nitrogen.

Form B was characterized as a methanolate (with 1 eq of methanol) with plate shaped crystals under microscope and distinctive XRPD. Crystallization of Form B provide high recovery yield and good ability for removing impurities. While Form B may not be the most desired form for pharmaceutical use due to the presence of methanol, the desirable purity and high yield of crystalline Form B from amorphous TP-434-046 can be translated into pure crystalline Form I, Form J or a mixture thereof for pharmaceutical use.

Form B is a co-solvate with MeOH (about 1 eq) and water.

Figure 3:
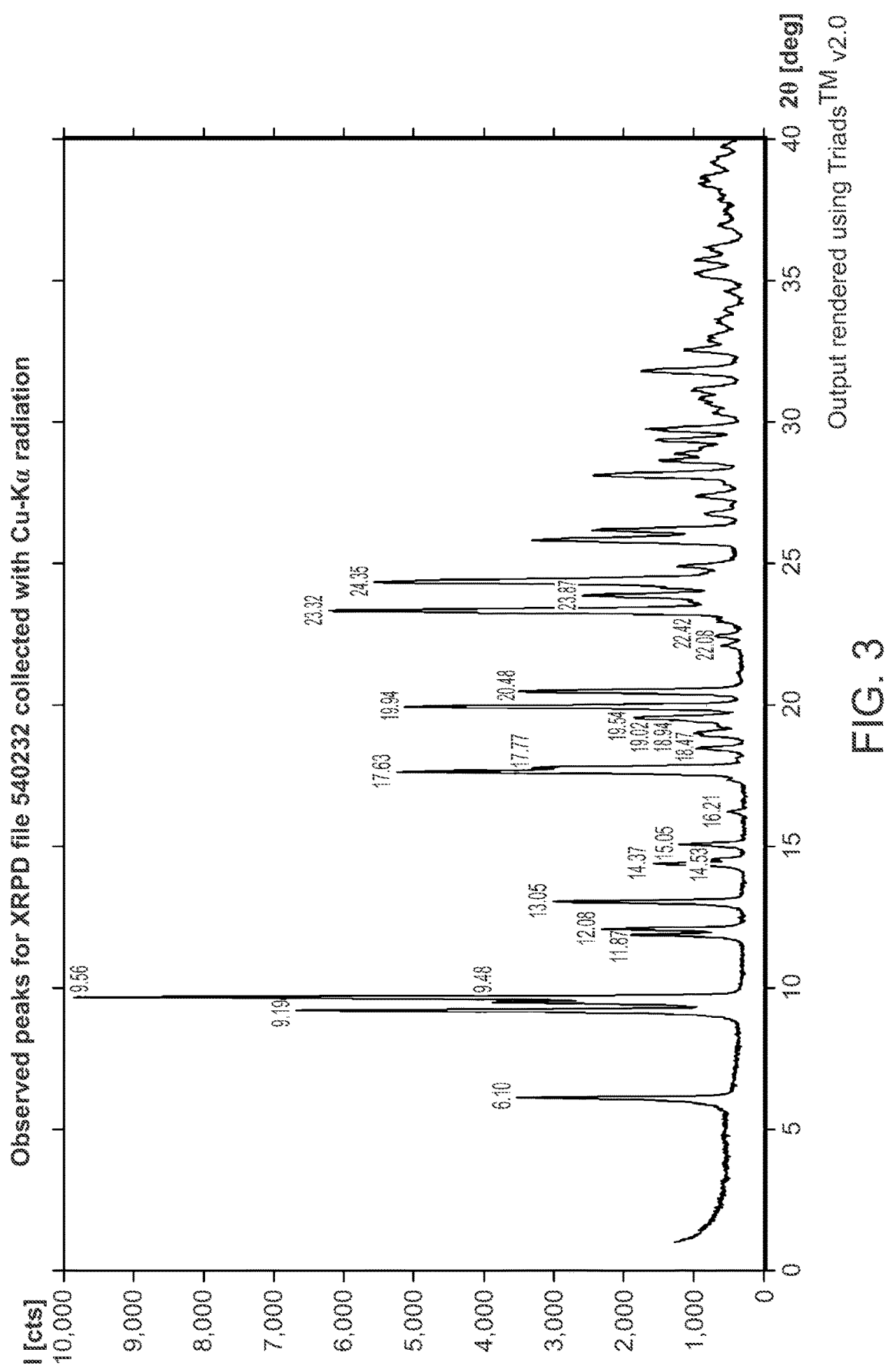
FIG. 3 is an XRPD pattern of Structural Formula 1—Form B.

The XRPD pattern of Form B IS depicted in FIG. 3 and the peaks are tabulated in Table 2.

TABLE 2

| °2θ | d space (Å) | Intensity (%) |
|---|---|---|
| 6.10 ± 0.20 | 14.467 ± 0.474 | 36 |
| 9.19 ± 0.20 | 9.612 ± 0.209 | 68 |
| 9.48 ± 0.20 | 9.325 ± 0.196 | 40 |
| 9.66 ± 0.20 | 9.149 ± 0.189 | 100 |
| 11.87 ± 0.20 | 7.450 ± 0.125 | 19 |
| 12.08 ± 0.20 | 7.319 ± 0.121 | 24 |
| 13.05 ± 0.20 | 6.781 ± 0.104 | 30 |
| 14.37 ± 0.20 | 6.159 ± 0.085 | 16 |
| 14.53 ± 0.20 | 6.091 ± 0.083 | 8 |
| 15.05 ± 0.20 | 5.880 ± 0.078 | 12 |
| 16.21 ± 0.20 | 5.462 ± 0.067 | 5 |
| 17.63 ± 0.20 | 5.027 ± 0.057 | 53 |
| 17.77 ± 0.20 | 4.989 ± 0.056 | 34 |
| 18.47 ± 0.20 | 4.801 ± 0.052 | 10 |
| 18.94 ± 0.20 | 4.683 ± 0.049 | 9 |
| 19.02 ± 0.20 | 4.662 ± 0.049 | 10 |
| 19.54 ± 0.20 | 4.538 ± 0.046 | 19 |
| 19.94 ± 0.20 | 4.449 ± 0.044 | 52 |
| 20.48 ± 0.20 | 4.333 ± 0.042 | 36 |
| 22.08 ± 0.20 | 4.022 ± 0.036 | 6 |
| 22.42 ± 0.20 | 3.962 ± 0.035 | 7 |
| 23.32 ± 0.20 | 3.811 ± 0.032 | 63 |
| 23.87 ± 0.20 | 3.726 ± 0.031 | 26 |
| 24.35 ± 0.20 | 3.653 ± 0.030 | 57 |

The TGA trace of Form B is depicted in FIG. 4A. The TG-FTIR measurement showed a release of MeOH and small amounts of water in the range of 50-150° C. (12.7 wt-% mass loss). The decomposition of the sample was detected above 200° C.

A DSC trace of Form B is shown in FIG. 4B. DSC measurement was carried out in a closed Au-crucible (closed under nitrogen flow). The sample was heated in the range of −50 to 205° C. showing a melting peak at 128° C. ($\Delta H_f$=56.3 J/g) and the beginning of the decomposition of the sample.

Example 3—Discovery of Form I/Form J

Preparation of Form I

Crystalline Form B was dissolved in EtOH (5 vol) and water (0.4 vol). The mixture was held at 35° C. for 4 hours then cooled to 30° C. and held for 2 hours. Additional solvents (0.3 vol of conc HCl and 0.1 vol of MeOH) were added and the solution was seeded with 5% crystalline Form A then cooled to room temperature. After stirring overnight at room temperature, crystals with a new shape were observed. The mixture was then heated to 35° C. for 1 hour and cooled to room temperature. The crystals were fully converted to the new form. This initial lot of new form was later found to be a mixture of Form J and Form I. Forms I and J appear as irregularly shaped hexagons, diamonds, or clusters under microscope and has a distinctive XRPD.

Example 4—Form I

Form I is a hemi-ethanolate containing about 0.5 eq (or about 3.5 wt %) of ethanol. The water content of Form I is about 3.4% (determined by KF).

Form I is an orthorhombic unit cell, spacegroup P212121, with unit cell parameters:

a=11.8 Angstroms
b=12.8 Å
c=39.9 Å
Vol=6024 Å$^3$.

Observed XRPD peaks for Form I are shown in FIG. 5, and listed in Table 3.

TABLE 3

| °2θ | d space (Å) | Intensity (%) |
|---|---|---|
| 4.44 ± 0.20 | 19.886 ± 0.895 | 11 |
| 7.22 ± 0.20 | 12.235 ± 0.339 | 100 |
| 7.80 ± 0.20 | 11.325 ± 0.290 | 88 |
| 8.19 ± 0.20 | 10.787 ± 0.263 | 32 |
| 8.71 ± 0.20 | 10.144 ± 0.232 | 11 |
| 9.59 ± 0.20 | 9.216 ± 0.192 | 10 |
| 10.41 ± 0.20 | 8.490 ± 0.163 | 44 |
| 11.11 ± 0.20 | 7.960 ± 0.143 | 56 |
| 11.62 ± 0.20 | 7.608 ± 0.130 | 12 |
| 12.17 ± 0.20 | 7.266 ± 0.119 | 25 |
| 13.08 ± 0.20 | 6.761 ± 0.103 | 13 |
| 13.52 ± 0.20 | 6.546 ± 0.096 | 21 |
| 13.78 ± 0.20 | 6.420 ± 0.093 | 19 |
| 14.49 ± 0.20 | 6.108 ± 0.084 | 9 |
| 15.00 ± 0.20 | 5.900 ± 0.078 | 30 |
| 15.33 ± 0.20 | 5.774 ± 0.075 | 11 |
| 15.70 ± 0.20 | 5.639 ± 0.071 | 22 |
| 15.86 ± 0.20 | 5.584 ± 0.070 | 17 |
| 16.47 ± 0.20 | 5.378 ± 0.065 | 33 |
| 17.12 ± 0.20 | 5.176 ± 0.060 | 17 |
| 17.47 ± 0.20 | 5.071 ± 0.058 | 10 |
| 17.79 ± 0.20 | 4.982 ± 0.056 | 11 |
| 18.79 ± 0.20 | 4.719 ± 0.050 | 18 |
| 19.29 ± 0.20 | 4.597 ± 0.047 | 9 |
| 19.96 ± 0.20 | 4.444 ± 0.044 | 22 |
| 20.44 ± 0.20 | 4.342 ± 0.042 | 35 |
| 20.91 ± 0.20 | 4.244 ± 0.040 | 17 |

Figure 6A:
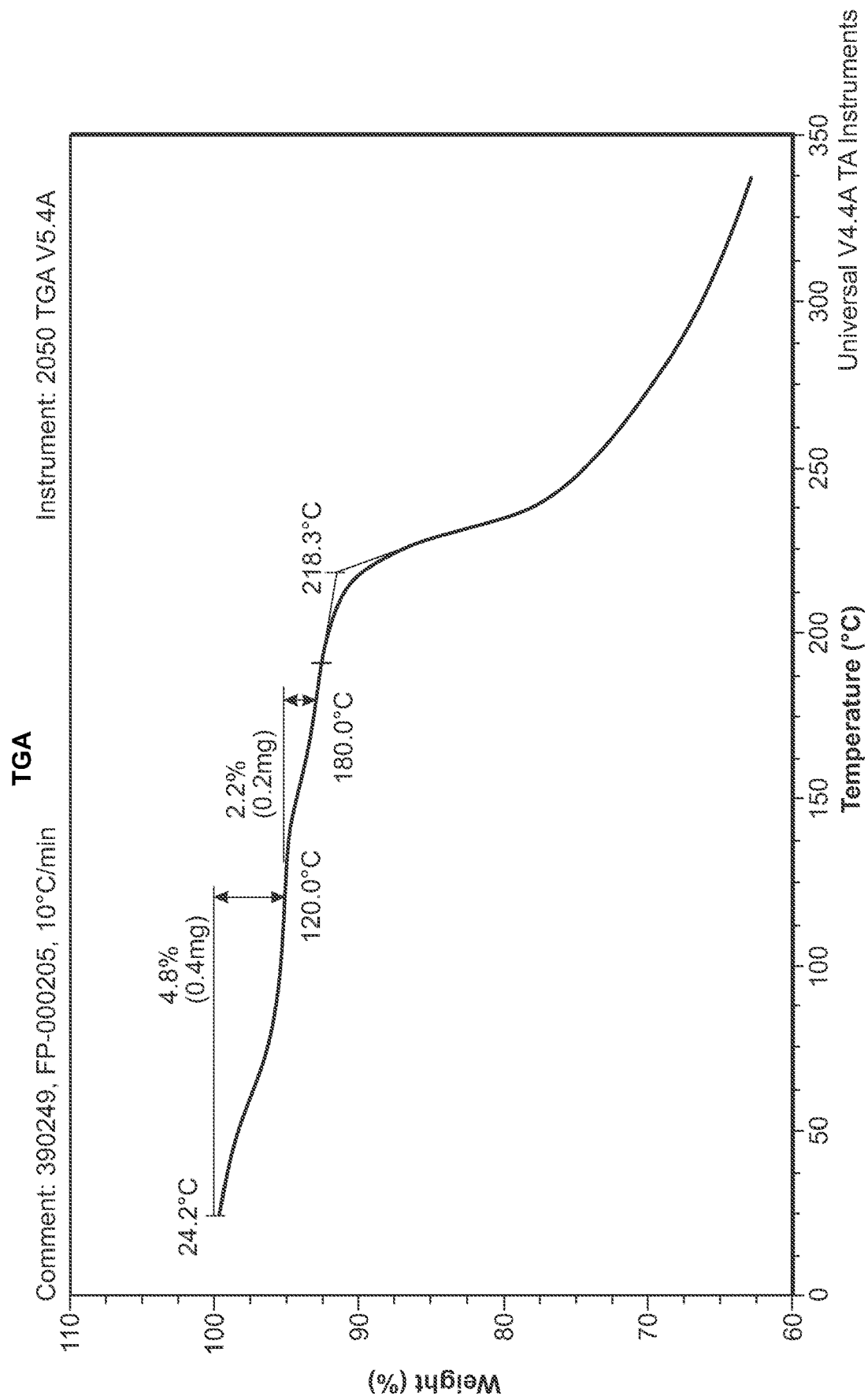
FIG. 6A is a TGA thermogram of Structural Formula 1—Form I.

By TGA, Form I exhibits approximately 4.8% weight loss from ambient to 120° C., followed by a weight loss of approximately 2.2% from 120 to 180° C., indicating loss of volatiles upon heating (FIG. 6A). The dramatic change in the slope of the TGA thermogram at approximately 218° C. is consistent with decomposition. Once the residual ethanol is lost, Form I can be converted into Form J.

Figure 6B:
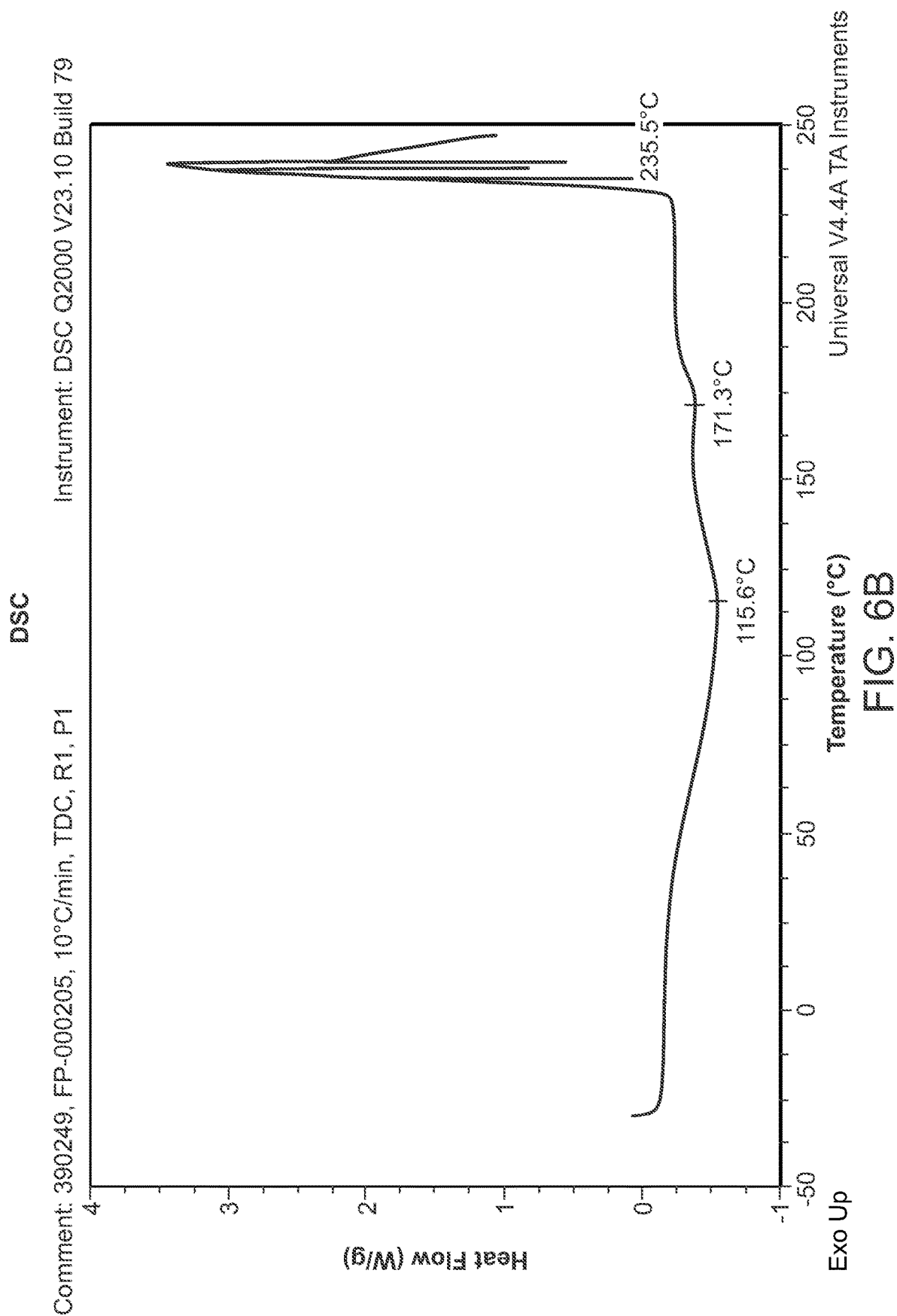
FIG. 6B is a DSC thermogram of Structural Formula 1—Form I

The DSC thermogram displays a broad, weak endotherm at approximately 116° C. which is concurrent with the first weight loss step by TGA due to the loss of volatiles. Another weak endotherm is observed at approximately 171° C. and likely corresponds to the second, smaller weight loss in TGA. A series of sharp overlapping endothermic and exothermic transitions observed above ~235° C. are likely due to decomposition (FIG. 6B).

Example 5—Form J (De-Solvated Form of Form I)

Form J was identified from a 1-month stability sample of Form I stored at 40° C./75% RH. Form J can be generated by exposing Form I under 40° C./75% RH or at room temperature with 75-85% RH until almost all residual ethanol is removed. Form J was determined to be the de-solvated form of Form I.

Form J is orthorhombic, spacegroup P212121 with unit cell parameters
a=11.8 Å
b=13.3 Å
c=38.5 Å
Vol=6060 Å$^3$.

Observed peaks for Form J are shown in FIG. 7 and listed in Table 4.

TABLE 4

| °2θ | d space (Å) | Intensity (%) |
|---|---|---|
| 4.58 ± 0.20 | 19.287 ± 0.842 | 14 |
| 7.02 ± 0.20 | 12.588 ± 0.358 | 93 |
| 7.80 ± 0.20 | 11.325 ± 0.290 | 100 |
| 8.07 ± 0.20 | 10.948 ± 0.271 | 19 |
| 8.76 ± 0.20 | 10.088 ± 0.230 | 19 |
| 9.19 ± 0.20 | 9.619 ± 0.209 | 8 |
| 9.57 ± 0.20 | 9.236 ± 0.193 | 12 |
| 10.25 ± 0.20 | 8.619 ± 0.168 | 53 |
| 11.00 ± 0.20 | 8.033 ± 0.146 | 34 |
| 11.35 ± 0.20 | 7.793 ± 0.137 | 9 |
| 11.85 ± 0.20 | 7.464 ± 0.126 | 20 |
| 12.15 ± 0.20 | 7.279 ± 0.119 | 12 |
| 13.29 ± 0.20 | 6.654 ± 0.100 | 33 |
| 13.60 ± 0.20 | 6.506 ± 0.095 | 34 |
| 14.09 ± 0.20 | 6.280 ± 0.089 | 11 |
| 14.98 ± 0.20 | 5.909 ± 0.078 | 39 |
| 15.27 ± 0.20 | 5.796 ± 0.075 | 21 |
| 15.45 ± 0.20 | 5.732 ± 0.074 | 16 |
| 15.64 ± 0.20 | 5.660 ± 0.072 | 8 |
| 16.21 ± 0.20 | 5.465 ± 0.067 | 29 |
| 16.39 ± 0.20 | 5.405 ± 0.066 | 24 |
| 17.04 ± 0.20 | 5.200 ± 0.061 | 21 |
| 17.59 ± 0.20 | 5.037 ± 0.057 | 18 |
| 17.80 ± 0.20 | 4.979 ± 0.055 | 10 |
| 18.45 ± 0.20 | 4.804 ± 0.052 | 7 |
| 18.84 ± 0.20 | 4.706 ± 0.050 | 12 |
| 19.17 ± 0.20 | 4.626 ± 0.048 | 11 |
| 20.10 ± 0.20 | 4.415 ± 0.043 | 28 |
| 20.63 ± 0.20 | 4.301 ± 0.041 | 17 |
| 21.53 ± 0.20 | 4.125 ± 0.038 | 23 |
| 21.92 ± 0.20 | 4.051 ± 0.037 | 32 |
| 22.13 ± 0.20 | 4.013 ± 0.036 | 58 |
| 22.52 ± 0.20 | 3.945 ± 0.035 | 21 |
| 23.22 ± 0.20 | 3.828 ± 0.033 | 61 |
| 23.58 ± 0.20 | 3.770 ± 0.032 | 18 |
| 24.02 ± 0.20 | 3.702 ± 0.030 | 30 |
| 24.41 ± 0.20 | 3.644 ± 0.029 | 23 |
| 25.28 ± 0.20 | 3.520 ± 0.027 | 34 |
| 26.08 ± 0.20 | 3.414 ± 0.026 | 28 |
| 26.35 ± 0.20 | 3.380 ± 0.025 | 25 |
| 26.78 ± 0.20 | 3.326 ± 0.024 | 23 |
| 27.21 ± 0.20 | 3.275 ± 0.024 | 13 |
| 27.41 ± 0.20 | 3.251 ± 0.023 | 12 |
| 27.90 ± 0.20 | 3.195 ± 0.022 | 29 |
| 28.78 ± 0.20 | 3.100 ± 0.021 | 14 |

Figure 8A:
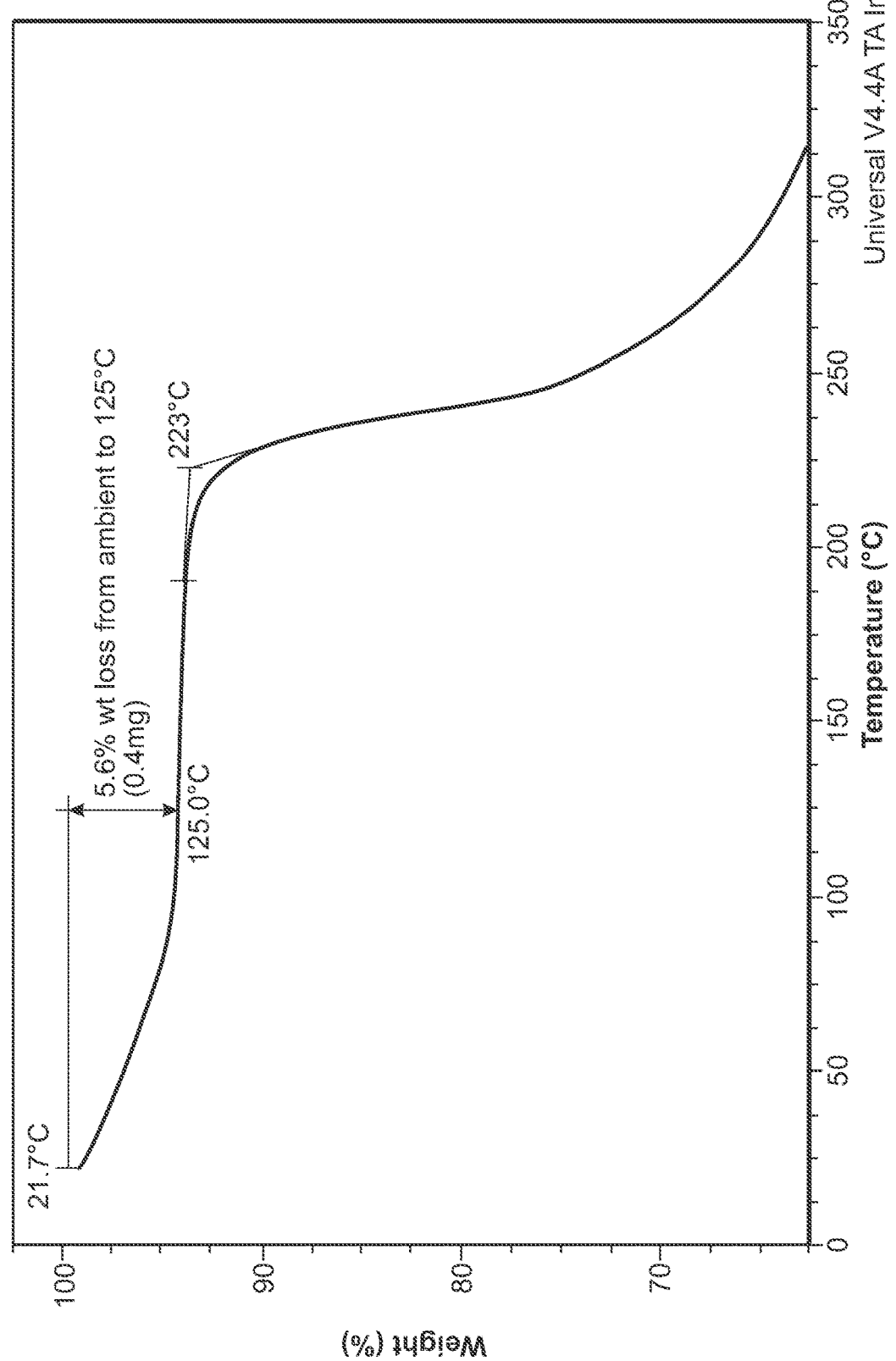
FIG. 8A is a TGA thermogram of Structural Formula 1—Form J.
Figure 8B:
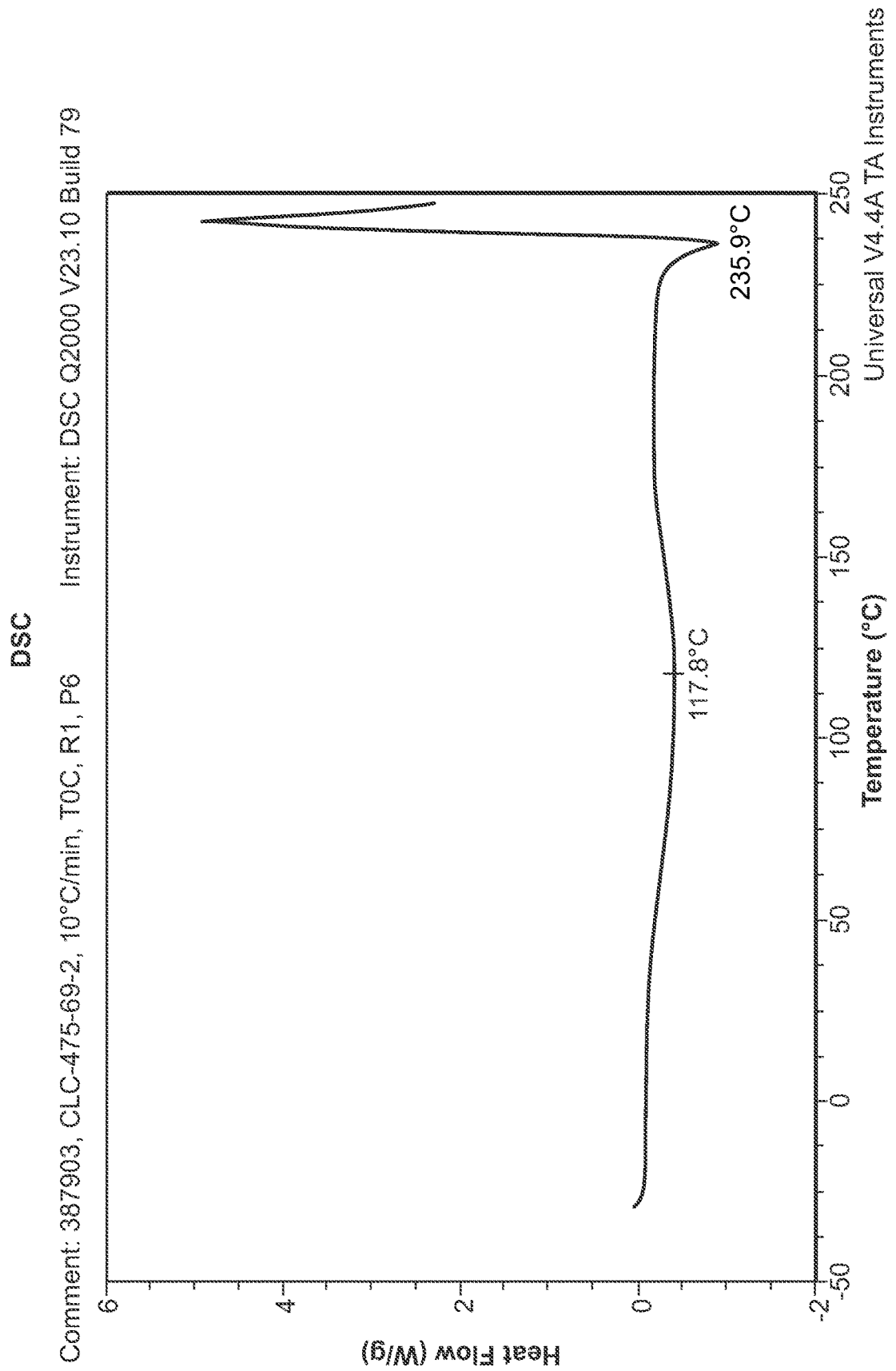
FIG. 8B is a DSC thermogram of Structural Formula 1—Form J.
Figure 9:
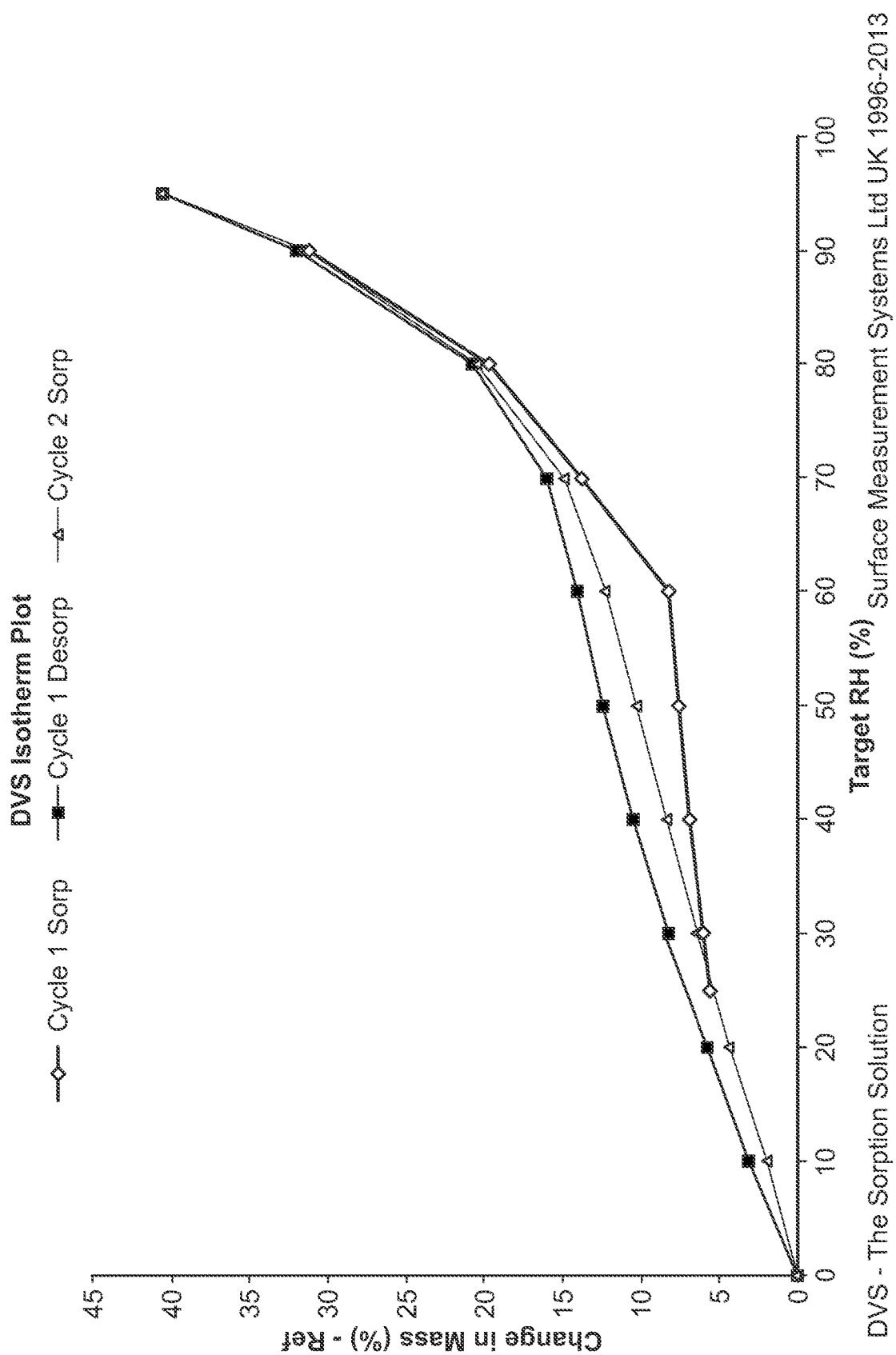
FIG. 9 is a DVS of Structural Formula 1—Amorphous Form
Figure 10:
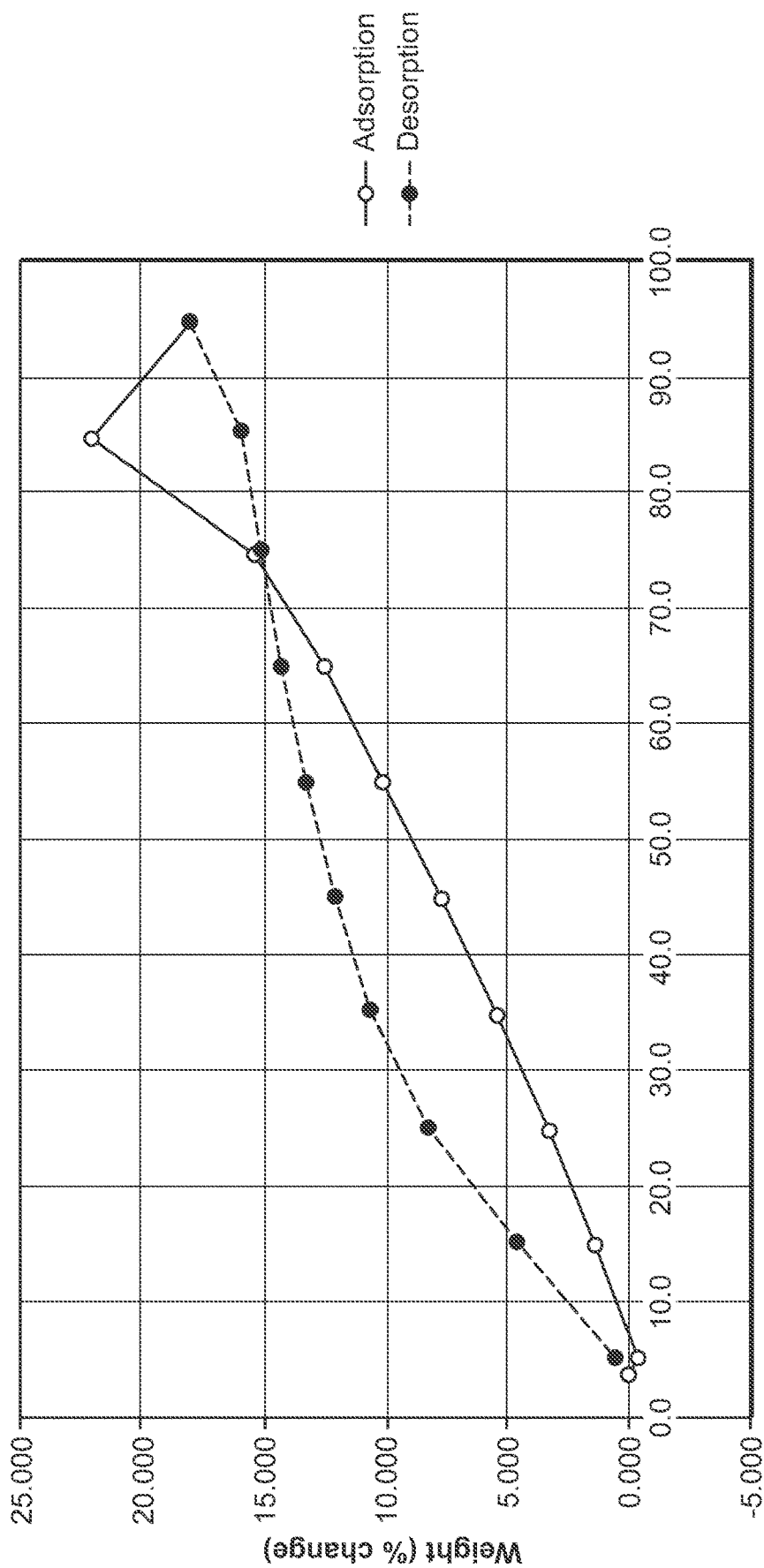
FIG. 10 is a DVS of Structural Formula 1—Form A
Figure 11:
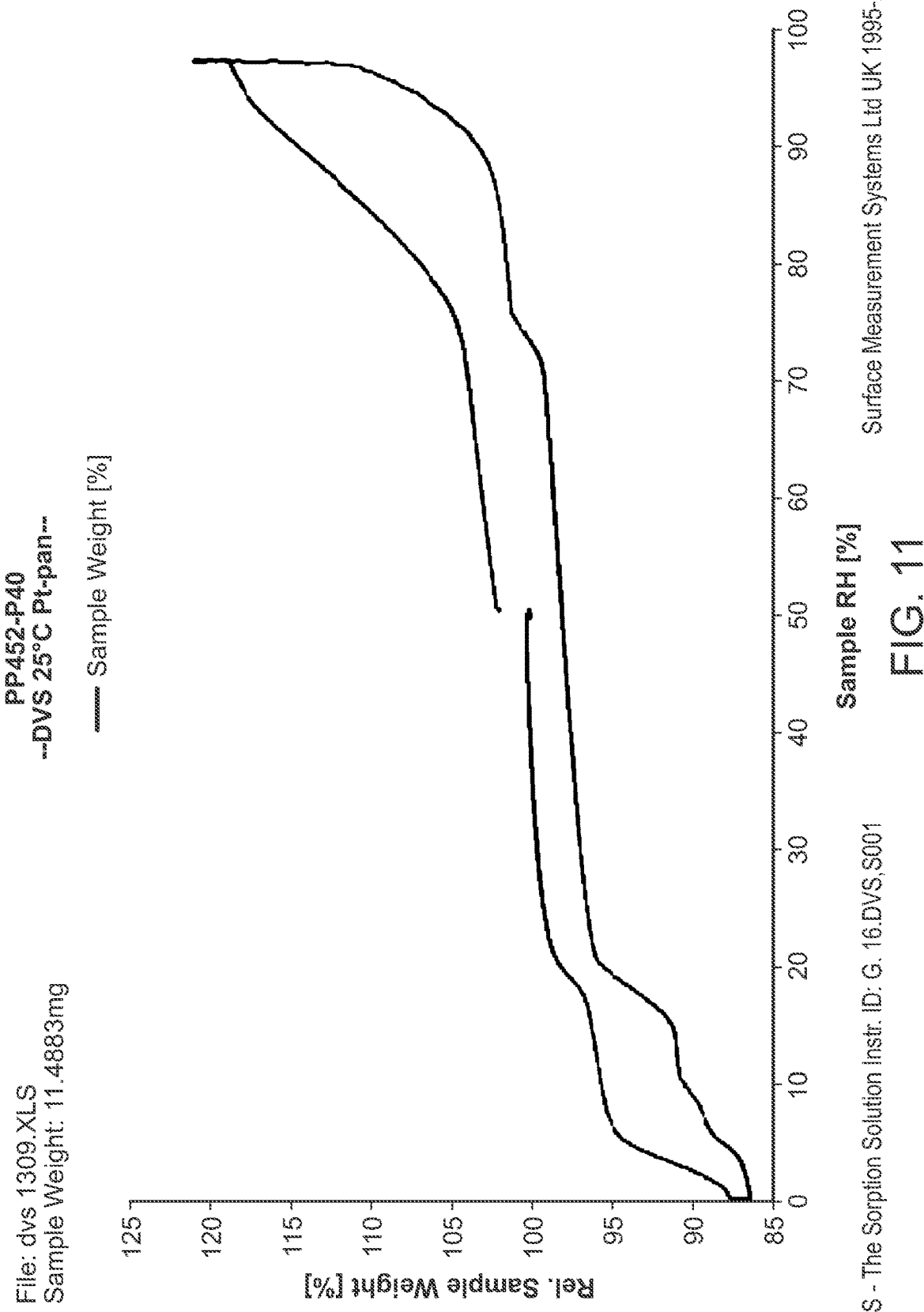
FIG. 11 is a DVS of Structural Formula 1—Form B
Figure 12:
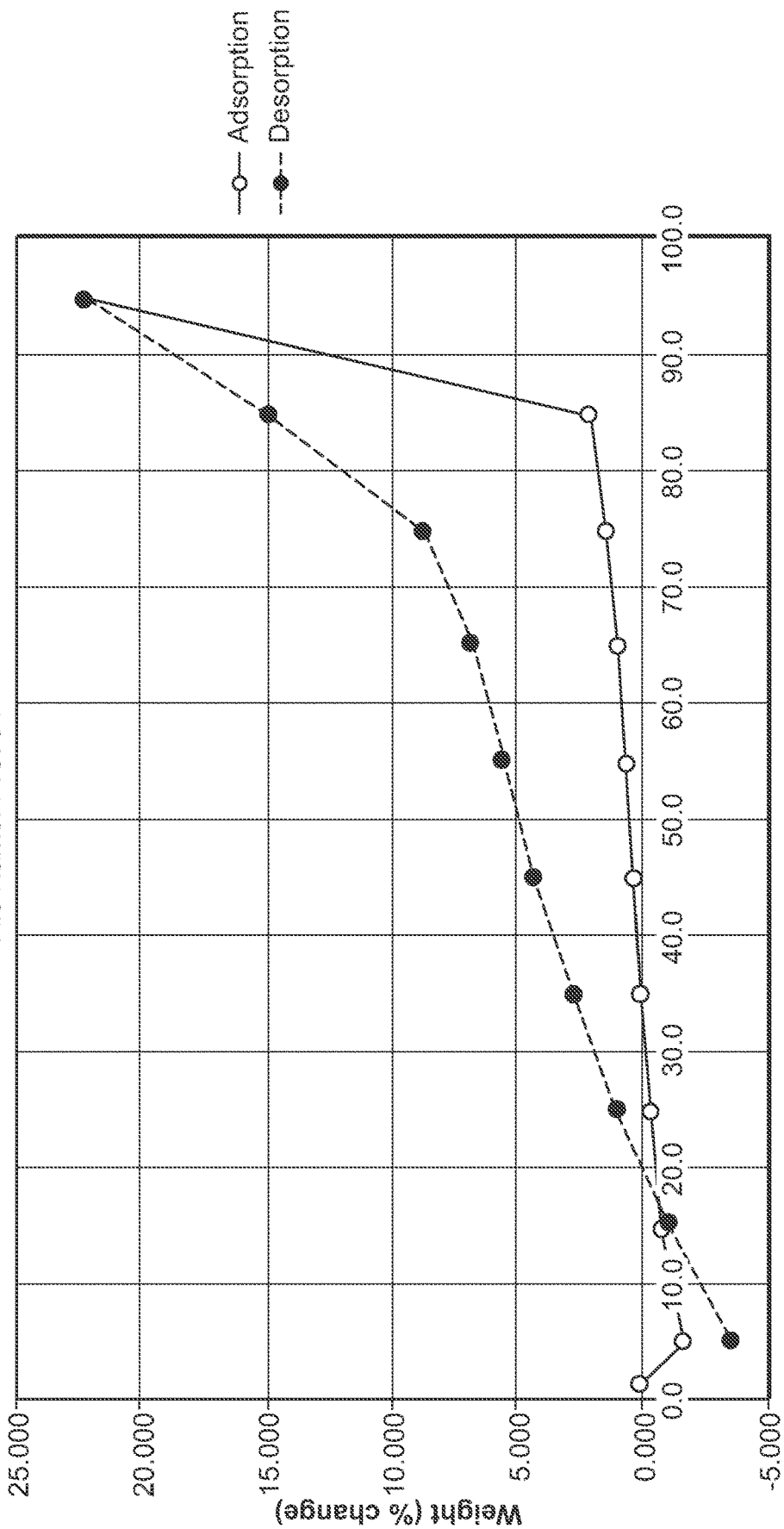
FIG. 12 is a DVS of Structural Formula 1—Form I
Figure 13:
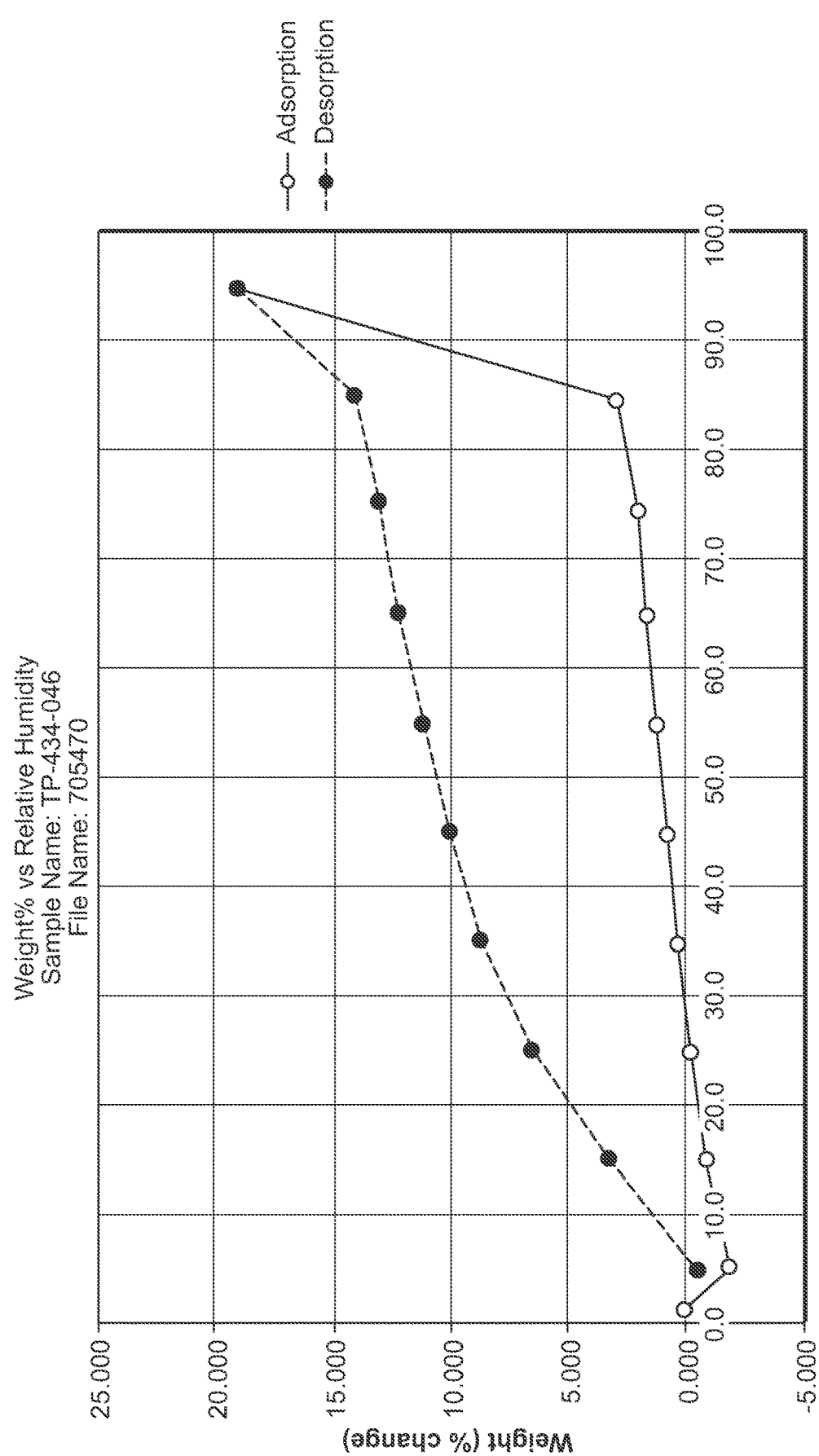
FIG. 13 is a DVS of Structural Form 1—Form J

By TGA, Form J exhibits approximately 5.6% weight loss from ambient to 125° C., indicating loss of volatiles upon heating (FIG. 8A). The dramatic change in the slope of the TGA thermogram at approximately 223° C. is consistent with decomposition.

The DSC thermogram (FIG. 8B) displays a broad endotherm at approximately 118° C. which is concurrent with the weight loss step by TGA due to the loss of volatiles. A weak, sharper endotherm is observed at approximately 236° C. and may be associated with a melt/decomposition.

Example 6—Relationship Between Form I and Form J

The unit cells of Form I and Form J are sufficiently different to call them different forms (see above). Form I and J have the same space group and have similar relative dimensions to likely be isostructural in their packing arrangement of the molecules. Form I can be completely converted to Form J by exposure to humidity and heat (e.g. under 45° C./75% RH or heating to 180° C.). The fact that mixtures of Form I and J are seen in many samples indicates that Form I and Form J represent different thermodynamic phases.

Example 7—Advantages of Crystalline Forms

Crystalline Forms A, B, I and J have many advantages over amorphohous. The amorphous material is very hygroscopic and can deliquite easily when exposed to moisture. The amorphous material is unstable and the rate of epimerizaton is much greater. See the data in Table 5, Table 6 and Table 7 below. The bis HCl salt of Structural Formula 1 contains fewer impurities when isolated as Forms A, B, I and J than when isolated as amorphous (See Table 8 below). In fact, the exceptional purity of Form B can be translated into highly pure crystalline Form I, crystalline Form J or a mixture of crystalline Forms I and J for pharmaceutical use. By using the procedures described herein for converting crystalline Form B into crystalline Forms I, crystalline Form J or a mixture thereof, crystalline Form I, crystalline Form J or a mixture thereof can be isolated as a composition ready for formulation as a pharmaceutical composition (e.g., acceptable purity, readily dissolvable and/or exhibiting good flow properties).

Among Forms A, I and J, Forms I and J were found to have advantages over Form A as the Active Pharmaceutical Ingredient (API). In general, they are thermodynamically more stable than other forms in the current crystallization systems and tolerate wider process/operation ranges; have higher isolation yields than Form A; are faster to filter and easier to dry than Form A; are much less hygroscopic between 5-85% RH than Form A; have higher bulk densities and better flow properties than Form A. The detailed data are discussed in the following.

Example 8—Epimerization Studies

Comparison of Form a, Form B and Amorphous at Room Temperature and 40° C.

The major degradant of the compound of Formula 1 (all forms) is the epimer at the C-4 carbon of the A-Ring of tetracycline core. Epimer increases from a 4-week stability study at both room temperature and 40° C. of amorphous form, Form A and Form B are summarized in Table 5. The epimer increases of amorphous form at both room temperature and 40° C. are much higher than those of Form A and B.

TABLE 5

Epimer increases in a 4-week Stability Study of Amorphous Form, Form A and Form B at Room Temperature (RT) and 40° C.

|  | Form A | | Form B Lot# | | Amorphous Form | |
|---|---|---|---|---|---|---|
|  | 2414-44-1 | | CLC-441-41 | | SC-452-106 | |
| Temperature | RT | 40° C. | RT | 40° C. | RT | 40° C. |
| Epimer increase | 0.31% | 2.14% | 0.34% | 3.65% | 0.96% | 8.18% |

Additional Epimerization Studies

Comparison of Forms a, B, I and J and Amorphous at 5° C. and Room Temperature

Stability testing was conducted over three months by placing the desired sample in a vial, capping the vial and then placing parafilm over the cap. The vials were stored at the designated temperature. The samples were analyzed by HPLC both at the beginning of testing and at the end of testing.

In one stability study, amorphous form was compared side-by-side with Form A and Form B. The epimer changes in the 3-month stability samples at both 5° C. and room temperature (RT) are summarized in Table 6. The epimer increases in the amorphous sample are 3.42% and 5.47% respectively at 5° C. and RT after 3 months, which are much greater than those seen for Forms A and B. These data demonstrated that amorphous form epimerizes much faster and is much less stable than Form A and B.

TABLE 6

Epimer increases in a 3-Month Stability Study of Amorphous Form, Form A and Form B at Room Temperature (RT) and 5° C.

|  | Form A | | Form B Lot# | | Amorphous Form | |
|---|---|---|---|---|---|---|
|  | 2414-44-1 | | CLC-441-41 | | SC-452-106 | |
| Temperature | 5° C. | RT | 5° C. | RT | 5° C. | RT |
| Epimer increase | 0.00% | 0.58% | 0.03% | 0.65% | 3.42% | 5.47% |

In another stability study, the stability of Forms A, I and J were compared. The desired stability samples were packaged in double PE bags with desiccant between the bags and then sealed in a foil bag. The stability samples were stored under the designated stability temperature. The samples were analyzed by HPLC at initiation of the testing and at three months.

The corresponding epimer changes in the 3-month stability samples at both 5° C. and room temperature (RT) are summarized in Table 7. Form I and J showed epimer amounts comparable to those seen for Form A.

TABLE 7

Epimer changes in a 3-Month Stability Study of Form A, Form I and Form J at Room Temperature (RT) and 5° C.

|  | Form A | | Form I Lot# | | Form J | |
|---|---|---|---|---|---|---|
|  | 924001N14 | | DL-509-1 | | CLC-475-72-3 | |
| Temperature | 5° C. | RT | 5° C. | RT | 5° C. | RT |
| Epimer changes | −0.14% | 0.29% | 0.02% | 0.75% | −0.04% | 0.07% |

The data in both stability studies demonstrated that crystalline forms A, B, I and J were more stable than amorphous form.

Example 9—Dynamic Vapor Sorption/Desorption (DVS)

Moisture sorption/desorption data were collected on a VTI SGA-100 Vapor Sorption Analyzer for Forms A, I and J. Sorption and desorption data were collected over a range from 5% to 95% RH at 10% RH increments under a nitrogen purge.

For Amorphous solid, Dynamic Vapor Sorption (DVS) was measured via a SMS (Surface Measurement Systems) DVS Intrinsic instrument. Sorption and desorption were collected using the following program: 25% RH-95% RH-0% RH-95% RH in 10% RH increments.

For Form B, Dynamic Vapor Sorption (DVS) was measured via a SMA (Surface Measurement Systems) DVS-1 water vapor sorption analyzer. Sorption and desorption were collected using the following program: 50% RH-0% RH-96% RH-50% RH in 5% RH/h increments.

The DVS Plots are shown in FIGS. 9-13 (amorphous, Form A, Form B, Form I and Form J, respectively). The DVS data below showed that amorphous TP-434-046 has the most weight gain when relative humidity increased from 25% RH to 95% RH: amorphous (about 35.5%), Form A (about 19.5%), Form B (about 11%), Form I (about 24.5%), Form J (about 21%). These data are generated from the absorption curve of the DVS as in most cases the form changed before desorption curve start.

Example 10—Impurity Purging Studies

The impurity purging abilities of slurry to slurry conversion of Form B to Form I/J as described herein are summarized below in Table 8 and compared with Forms A and B crystallization processes described herein. Of note, the precipitation to generate the amorphous form does not purge any of the impurities. Form B provides the necessary reduction in the impurity M-16 (TP-6773), which is difficult to remove. In addition, other impurities are also removed at the necessary levels by Form B crystallization (see, e.g., NMP and TP-630). While Form B may not be the most desirable Form described herein to use as an API because it is a methanolate, the high impurity purging ability is advantageous for conversion to thermodynamically stable Form I, Form J or a mixture thereof.

TABLE 8

| Impurity | Impurity Purging (Reduction of Impurity Level) | | | |
|---|---|---|---|---|
| | Amorphous Form Precipitation | Form A crystallization | Form B crystallization | Slurry Form B to Form I/J |
| M − 16 (TP-6773) | No purging | 5-8% | 25-28% | Increased ≈10% |
| Epimer (TP-498) | No purging | Up to 40% | 70% | 40-80% |
| M − 18 (TP-5799) | No purging | 90% | 30-60% | 25-40% |
| TP-034 | No purging | 90% | 50-79% | 50-80% |
| M − 2 (TP-4705) | NA | NA | 50% | 90% |
| M + 14 (TP-363) | NA | >95% | 62% | 85% |
| TP-630 | 54% | >95% | >99% | >99% |
| NMP | 97% | >95% | >99% | >99% |
| M + 94 (TP-3978) | NA | NA | >98% | 61% |

The structures of the impurities are set forth below:

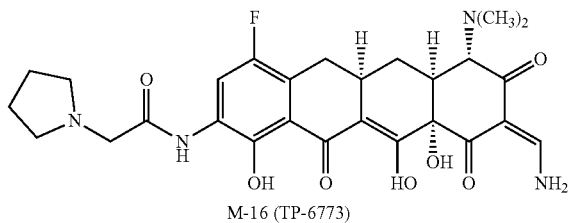

M-16 (TP-6773)

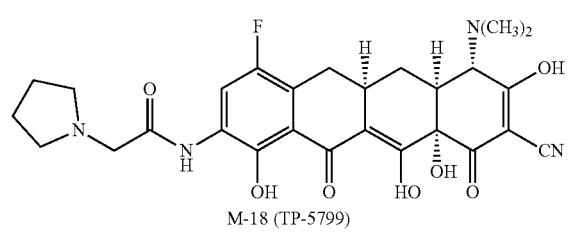

M-18 (TP-5799)

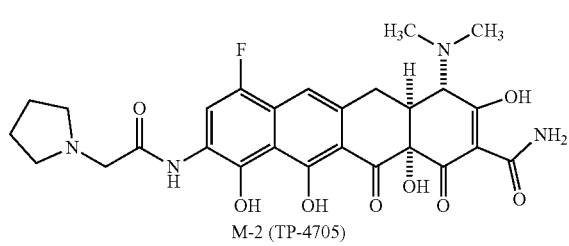

M-2 (TP-4705)

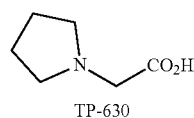

TP-630

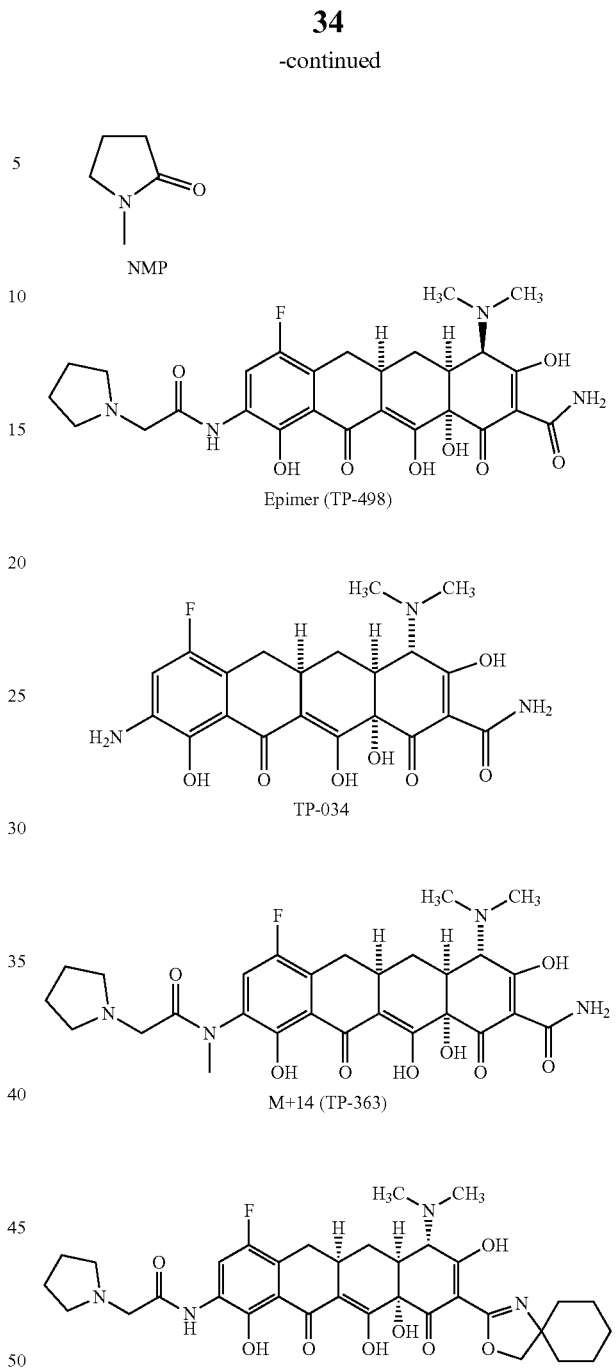

Example 11—Large Scale Batches of Form I and Form J

50-g Scale-Up Batch

A 50-g scale-up of the slurry-to-slurry process was performed. Form B was converted to the new form overnight. The supernatant concentration after 18 hours was 21 mg/g (TP-434 free base). The solids were filtered (fast filtration), washed with ethanol (1 vol) and dried in vacuum oven at 26° C. Scheme 1 summarizes the results from this experiment. XRPD pattern of this material confirmed that it was mostly Form I with minor Form J. The freebase (FB) potency of TP-434 was determined by HPLC weight/weight assay using TP-434 reference standard.

Scheme 1. 50-g Scale up of Slurry-to-Slurry Process to Prepare Form I

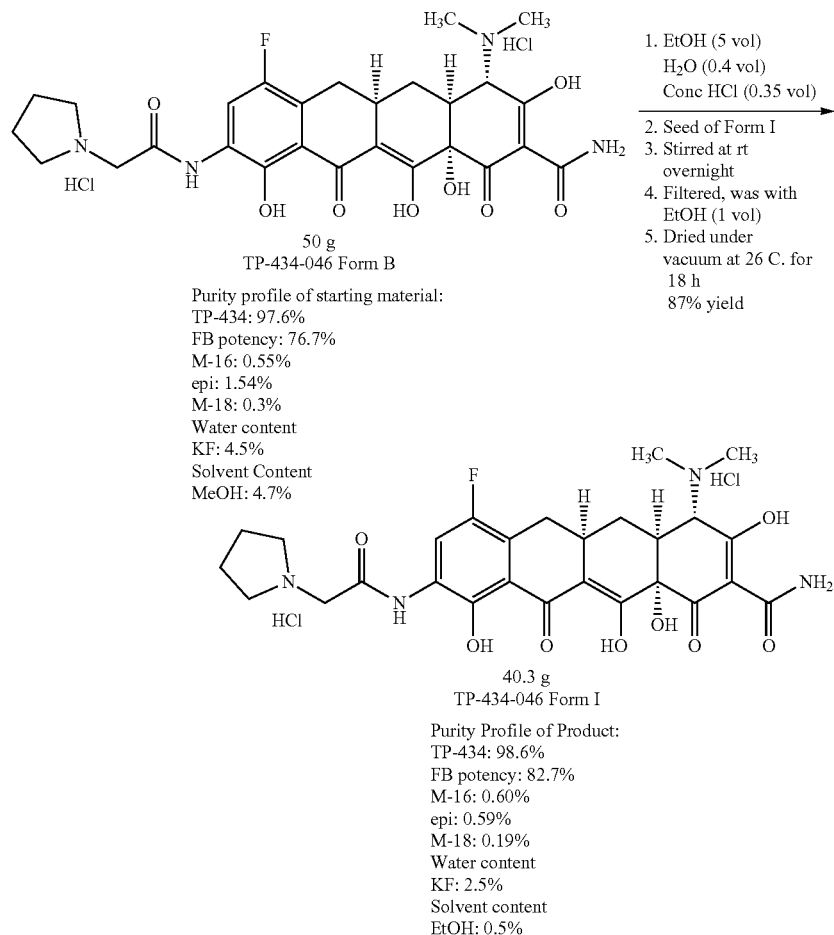

50 g
TP-434-046 Form B

Purity profile of starting material:
TP-434: 97.6%
FB potency: 76.7%
M-16: 0.55%
epi: 1.54%
M-18: 0.3%
Water content
KF: 4.5%
Solvent Content
MeOH: 4.7%

1. EtOH (5 vol)
   H₂O (0.4 vol)
   Conc HCl (0.35 vol)
2. Seed of Form I
3. Stirred at rt overnight
4. Filtered, was with EtOH (1 vol)
5. Dried under vacuum at 26 C. for 18 h
   87% yield 40.3 g
TP-434-046 Form I Purity Profile of Product:
TP-434: 98.6%
FB potency: 82.7%
M-16: 0.60%
epi: 0.59%
M-18: 0.19%
Water content
KF: 2.5%
Solvent content
EtOH: 0.5%

100-g Scale-Up Batch

Preparation of Form I was scaled up using 100 g of Form B. The experiment was carried out by adding Form B into a solution of 5 vol of EtOH, 0.4 vol of water, 0.4 of conc. HCl followed by charging Form I seeds (2.5 wt % seed loading) and a total of 85 g of Form I was isolated. Scheme 2 summarizes the data. The purity of Form I was consistent with previous batches.

Scheme 2. Form B slurry to Form I 100-g scale-up

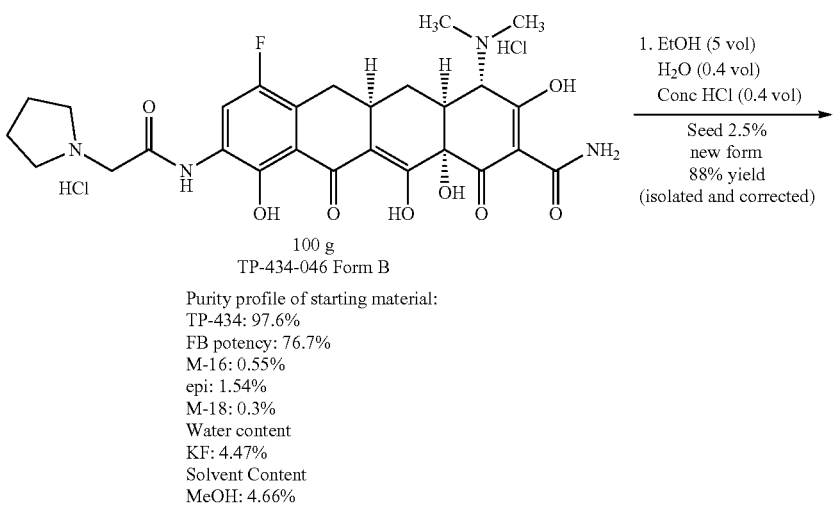

100 g
TP-434-046 Form B

Purity profile of starting material:
TP-434: 97.6%
FB potency: 76.7%
M-16: 0.55%
epi: 1.54%
M-18: 0.3%
Water content
KF: 4.47%
Solvent Content
MeOH: 4.66%

1. EtOH (5 vol)
   H₂O (0.4 vol)
   Conc HCl (0.4 vol)

Seed 2.5%
new form
88% yield
(isolated and corrected)

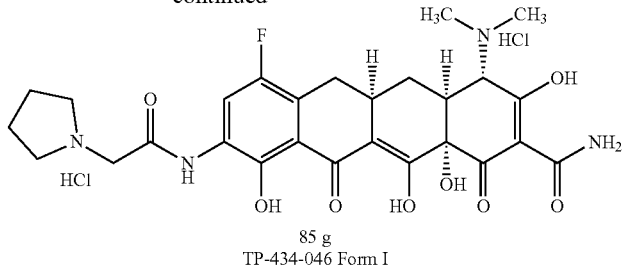

85 g
TP-434-046 Form I

Purity Profile of Product:
TP-434: 98.58%
FB potency: 81.0%
M-16: 0.61%
epi: 0.61%
M-18: 0.2%
Water content
KF: 4.2%
Solvent content
EtOH: 3.3%

300-g Scale-Up Batch

A 300-g scale slurry to slurry conversion from Form B to Form I was performed. The batch overview is presented in Scheme 3:

Scheme 3. 300-g scale up of Form I Process 300 g (Form B)
TP-434-046

M-16: 0.44%
epi: 1.57%
M-18: 0.3%
TP-434: 97.1%
FB Potency: 75.6%
MeOH: 4.66%
KF: 4.47%

5 vol EtOH
0.4 vol H$_2$O
0.4 vol HCl

Seeds 2.5 wt %
Form I
91% yield
(isolated and corrected)

258 g (Form I)
TP-434-046

M-16: 0.52%
epi: 0.76%
M-18: 0.24%
TP-434: 98.1%
FB Potency: 81.8%
EtOH: 3.5%
KF: 3.54%

The rate of the 300-g scale crystallization was slower than expected. After overnight stirring at room temperature, the supernatant concentration for Form I crystallization usually stands at 8-15 mg/mL of free base. For the 300-g scale batch however, this concentration was 39 mg/mg. Cooling the suspension to 10° C., then 0° C., did not lower the concentration as fast as the equivalent operation for Form A. After 30 hours overall time, 1 volume of EtOH was added to the suspension at 0° C. The batch was allowed to stir at room temperature up to 48 hours total time. At this point, the concentration reached 11 mg/mL and the batch was filtered, washed and the product dried in vacuum oven overnight to afford TP-434-046 (Form I)

664-g Scale-Up Batch

Starting with Form B (664 g), the scale-up was carried out using the current Form B to Form I conversion procedure to afford TP-434-046 (575 g, 84% yield, containing 3.1% EtOH and 4.5% water) after drying in a vacuum oven. The batch overview is shown in Scheme 4. The XRPD was consistent with Form I with some Form J.

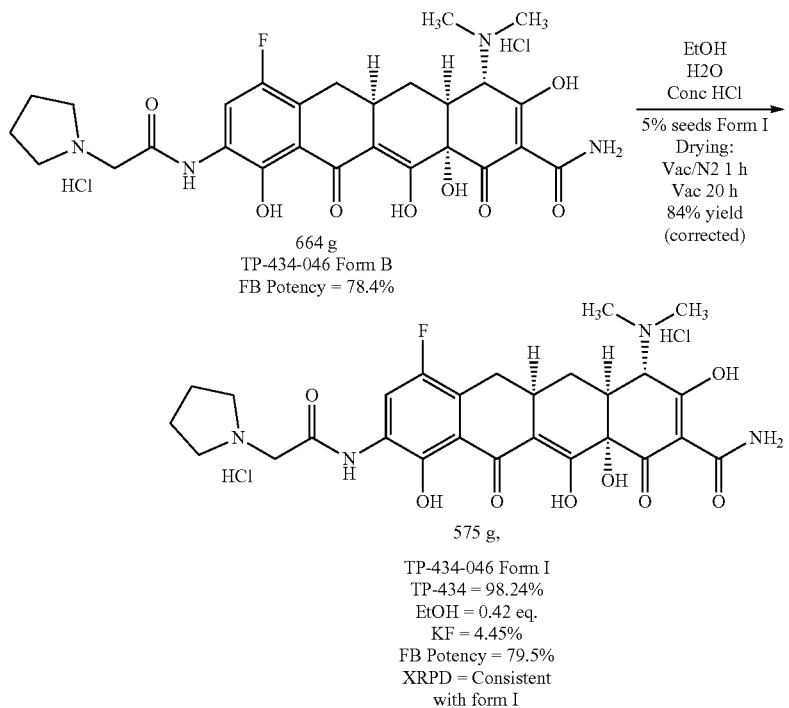

1.83-kg Scale-Up Batch

A Scale-up batch was made starting with 1.83 kg of Form B. The detailed procedure is described in the followings.

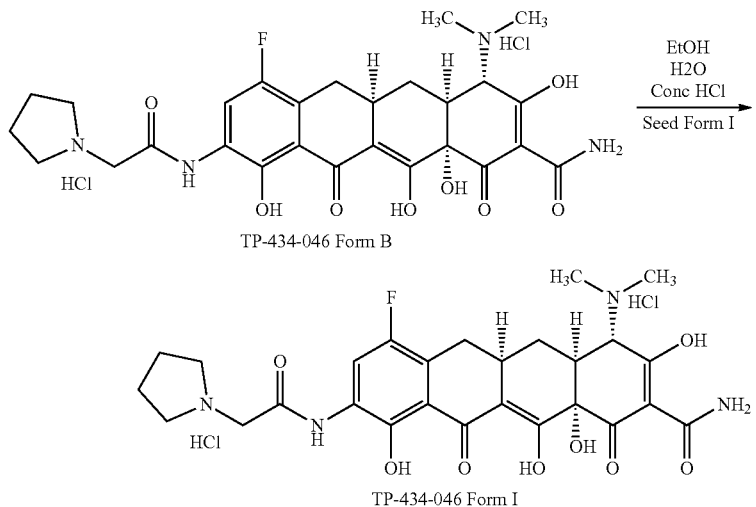

TABLE 9

| Material | Qty | MW | Mole eq. |
|---|---|---|---|
| TP-434-046 form B | 1830 g | 631.5 | 1.0 |
| EtOH 200 proof | 9150 mL | — | 5 V |
| Water-HPLC grade | 732 mL | — | 0.4 V |
| Conc HCl | 732 mL | — | 0.4 V |
| TP-434-046 form I seeds | 90 g | 631.5 | 5% wt |
| EtOH 200 proof | 5490 mL | — | 3 V |
| EtOH 200 proof | 3294 mL | — | 1.8 V |
| Water | 183 mL | — | 0.1 V |
| Conc HCl | 183 mL | — | 0.1 V |

1. To a 20 L reactor, charge EtOH (9150 mL), H$_2$O (732 mL) and concentrated HCl (732 mL). Note: Filtered the solution through the 0.22-μm filter prior to use.
2. Charge TP-434-046 form B (1830 g) in one portion and stir for 5 minutes to allow the solution to reach saturation.
3. Seed with form I (90 g) in one portion and stir at room temperature overnight 18 hours.
4. Check the Microscope, form B convert into Form I. Note: Confirm FORM I
5. Supernatant wt/wt assay is 1.77% using HPLC.
6. Add ethanol (5490 mL, 2 vol) over 3 hours. Note: Filter the solution through the 0.22-μm filter prior to use.
7. Stir the reaction mixture one more hour at room temperature.
8. Filter and collect the solids by 18-inch crock filter.
9. Then rinse the cake with 3660 mL of a rinsing solution made up of the initial solvent ratio (3294 mL EtOH/183 mL H$_2$O/183 mL conc HCl). Note: Filter the solution through the 0.22 μm filter prior to use.
10. Dry under nitrogen flow for overnight [EtOH (By HNMR): 3.63 wt %; KF: 6.27%]
11. Dry under vacuum oven to get constant weight at 25° C.
   EtOH (By HNMR): 3.45 wt %
   KF: 3.83%

Formation of Form I in Pilot Plant

Crude TP-434-046 was crystallized to give Form B, followed by slurry-to-slurry conversion of Form B to Form I/J.

Form B was charged into a mixture of EtOH/water/conc. HCl (5V/0.4V/0.4V) and stirred between 15° C. to 25° C. (targeting 21° C.) for 5 to 15 minutes (targeting 10 min) followed by the addition of Form I seeds (5 wt %). The mixture was stirred between 18° C. to 23° C. (targeting 21° C.) for 10 to 18 hours (targeting 14 hours). A sample was taken and analyzed for supernatant concentration and microscope. If the supernatant concentration was ≤6.0% and exclusive formation of Form I/J confirmed by microscope, ethanol (3V) was added over a minimum of 3 hours between 18° C. to 23° C. (targeting 21° C.). The mixture was then stirred for minimum of 1 hour before filtering.

In the first production, after the Form B slurry was seeded with Form I and stirred for 14 hours at 21° C. with stirring rate of 80 rpm, microscope showed a mixture of Form A and Form I/J. In order to speed up the conversion of Form A to Form I in production of FP-000205, the temperature was increased from 21° C. to about 22.5° C. (still within the defined temperature range of 18° C. to 23° C.) and the stirring speed was increased from 80 rpm to 120 rpm. Within 6 hours, all From A was converted to Form I. The supernatant concentration of TP-434-046 was 3.6%, meeting the specification of ≤6.0%. Ethanol (3V) was charged over 3 hours and the mixture was stirred for about 10 hours before filtering.

To avoid the formation of Form A and increase the rate of Form A to Form I/J conversion in case Form A does form, some modifications were made for the next two productions. The aging temperature and duration were both increased from between 18° C. to 23° C. (targeting 21° C.) for 10 to 18 hours (targeting 14 hours) to between 18° C. to 25° C. for 24 to 36 hours (targeting 24 hours); while targeting the upper part of the temperature range in the first 12 hours and targeting 21° C. in the second 12 hours.

The productions of the last two batches were executed according to the revised procedure. After the seeded mixtures were stirred at about 24° C. for about 12 hours, no presence of Form A was detected by microscope in either batch. After continuously stirring for 12 hours at 21° C., samples were taken and the supernatant concentrations were 2.5% and 2.8% respectively. After anti-solvent (EtOH 3V) addition over 3 hours, the mixture in 2nd batch was stirred for about 8 hours and the mixture in third batch was stirred for about 3 hours before filtration.

The brief summary of results on yield, XRPD, residual solvent, particle size and HPLC purity are combined in Table 10.

TABLE 10

Summary of Yields, XRPD, Residual Solvents, Particle size and HPLC purity of the Three Pilot Plant Batches

| Batch# | Yield | XRPD Interpretation | EtOH/KF (IPC data) | D10/D50/D90 (μm) | HPLC Analysis TP-434/M − 16/Epimer/ M − 2/M − 18/TP-034 |
|---|---|---|---|---|---|
| 1 | 87.9% | Consistent with Form I | 3.2%/5.8% (3.65%/5.1%) | 28.6/60.7/154.0 | 98.14/0.75/0.63/<0.05/ 0.42/0.06 |
| 2 | 80.3% | Consistent with Form I plus Form J | 3.5%/4.5% (3.43%/3.6%) | 89.8/137.2/211.9 | 97.97/0.87/0.83/ND/ 0.23/0.10 |
| 3 | 77.5% | Consistent with Form I plus Form J | 2.8%/4.6% (3.18%/5%) | 111.8/172.3/264.8 | 97.79/0.89/0.73/ND/ 0.38/0.21 |

Based on XRPDs data, Batch 1 contains only Form I, as demonstrated by the smooth shoulder for the first peak of Form I around 7° Θ. Batch 2 is consistent with Form I plus minor Form J, as demonstrated by the widened shoulder of the first peak of Form I around 7° Θ. Batch 3 contains more Form J, as demonstrated by the peak on the shoulder of the first peak of Form I around 7° Θ. All three registration batches met the XRPD spec defined as "consistent to Form I, Form J, or a mixture of Forms I and J."

With respect to Batch 1, which contains pure Form I, the formation of Form A as transient kinetic form during the Form B to Form I conversion may have affected the product XRPD and particle size. The particles in Batch 1 are mostly composed of smaller well-defined individual crystals, while the particles in Batch 2 and Batch 3 are composed with large crystals containing clusters of individual crystals. The morphologies of crystals of the three batches were also confirmed by polarized light microscopy on the isolated products (data not shown). The observations under microscope were also confirmed by the particle size distribution data where the D50 of Batch 1 is less than half of what were in Batch 2 and Batch 3, and much wilder particle size distribution was observed in Batch 1 (data not shown).

TGA and DSC analyses of the three batches were substantially identical.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A crystalline form of the bis-HCl salt of a compound represented by Structural Formula 1:

(1)

[chemical structure]

wherein the crystalline form is Form J and is characterized by at least three x-ray powder diffraction peaks at 2θ angles selected from the following values ±0.2°: 7.02°, 7.80°, 22.13°, and 23.22°, and
wherein the compound of Structural Formula (1) is in the form of a hydrate.

2. The crystalline form of claim 1, wherein the crystalline form is characterized by at least four x-ray powder diffraction peaks at 2θ angles selected from the following values ±0.2°: 7.02°, 7.80°, 10.25°, 22.13°, and 23.22°.

3. The crystalline form of claim 1, wherein the crystalline form is characterized by at least five x-ray powder diffraction peaks at 2θ angles, wherein
at least three x-ray powder diffraction peaks are selected from the following values ±0.2°: 7.02°, 7.80°, 22.13°, and 23.22°, and the remainder of the peaks is selected from the following values ±0.2°: 10.25°, 11.00°, 13.29°, 13.60°, 14.98°, 21.92°, 24.02° and 25.28°.

4. The crystalline form of claim 1, wherein the crystalline form is characterized by x-ray powder diffraction peaks at 2θ angles of the following values ±0.2°: 7.02°, 7.80°, 10.25°, 22.13°, and 23.22°.

5. The crystalline form of claim 1, wherein the crystalline form is characterized by x-ray powder diffraction peaks at 2θ angles of the following values ±0.2°: 7.02°, 7.80°, 10.25°, 11.00°, 13.29°, 13.60°, 14.98°, 21.92°, 22.13°, 23.22°, 24.02° and 25.28°.

6. The crystalline form of claim 1, wherein the crystalline form is characterized by x-ray powder diffraction peaks at 2θ angles of the following values ±0.2°: 7.02°, 7.80°, 10.25°, 11.00°, 11.85°, 13.29°, 13.60°, 14.98°, 15.27°, 16.21°, 16.39°, 17.04°, 20.10°, 21.53°, 21.92°, 22.13°, 22.52°, 23.22°, 24.02°, 24.41°, 25.28°, 26.08°, 26.35°, 26.78°, and 27.90°.

7. The crystalline form of claim 1, wherein the crystalline form is characterized by an x-ray powder diffraction pattern in accordance with that depicted in FIG. 7.

8. A crystalline form of the bis-HCl salt of a compound represented by Structural Formula 1:

(1)

[chemical structure]

wherein
the crystalline form is Form B and is characterized by at least three x-ray powder diffraction peaks at 2θ angles selected from the following values ±0.2°: 9.19°, 9.66°, 23.32°, and 24.35°,
wherein the compound represented by Structural Formula (1) is a co-solvate of water and methanol.

9. The crystalline form of claim 8, wherein the crystalline form is characterized by at least four x-ray powder diffraction peaks at 2θ angles selected from the following values ±0.2°: 9.19°, 9.66°, 17.63°, 23.32°, and 24.35°.

10. The crystalline form of claim 8, wherein the crystalline form is characterized by at least five x-ray powder diffraction peaks at 2θ angles,
wherein at least three x-ray powder diffraction peaks are selected from the following values ±0.2°: 9.19°, 9.66°, 23.32°, and 24.35°, and the remainder of the peaks is selected from the following values ±0.2°: 6.10°, 9.48°, 13.05°, 17.63°, 17.77°, 19.94°, and 20.48°.

11. The crystalline form of claim 8, wherein the crystalline form is characterized by x-ray powder diffraction peaks at 2θ angles of the following values ±0.2°: 9.19°, 9.66°, 17.63°, 23.32°, and 24.35°.

12. The crystalline form of claim 8, wherein the crystalline form is characterized by at least five x-ray powder diffraction peaks at 2θ angles,
wherein at least three x-ray powder diffraction peaks are selected from the following values ±0.2°: 9.19°, 9.66°, 23.32°, and 24.35°, and the remainder of the peaks is selected from the following values ±0.2°: 6.10°, 9.48°, 13.05°, 17.63°, 17.77°, 19.94°, 20.48°, and 23.87°.

13. The crystalline form of claim 8, wherein the crystalline form is characterized by x-ray powder diffraction peaks at 2θ angles of the following values ±0.2°: 6.10°, 9.19°, 9.48°, 9.66°, 12.08°, 13.05°, 17.63°, 17.77°, 19.54°, 19.94°, 20.48°, 23.32°, 23.87°, and 24.35°.

14. The crystalline form of claim 8, wherein the crystalline form is characterized by an x-ray powder diffraction pattern in accordance with that depicted in any of FIG. 3.

15. A pharmaceutical composition, comprising the crystalline form of claim 1 and a pharmaceutically acceptable carrier.

16. A method for treating or preventing an infection caused by bacteria, the method comprising administering to a subject in need thereof a therapeutically or prophylactically effective amount of the crystalline form of claim 1.

17. The method of claim 16, wherein the infection is caused by a Gram-positive bacterium.

18. The method of claim 16, wherein the infection is caused by a Gram-negative bacterium.

19. The method of claim 16, wherein the infection is complicated intra-abdominal infection.

20. The method of claim 19, wherein the subject is a human.

\* \* \* \* \*